United States Patent
Adams

(10) Patent No.: US 11,446,104 B2
(45) Date of Patent: Sep. 20, 2022

(54) MANUAL RELEASE ASSEMBLY FOR ROBOTIC SURGICAL TOOL

(71) Applicant: Ethicon LLC, Guaynabo, PR (US)

(72) Inventor: Eric Adams, Pittsboro, NC (US)

(73) Assignee: CILAG GMBH INTERNATIONAL, Zug (CH)

( * ) Notice: Subject to any disclaimer, the term of this patent is extended or adjusted under 35 U.S.C. 154(b) by 1365 days.

(21) Appl. No.: 15/794,596

(22) Filed: Oct. 26, 2017

(65) Prior Publication Data
US 2019/0125468 A1 May 2, 2019

(51) Int. Cl.
*A61B 34/00* (2016.01)
*A61B 34/30* (2016.01)
*A61B 17/00* (2006.01)
*F16H 37/12* (2006.01)
(Continued)

(52) U.S. Cl.
CPC ........ *A61B 34/71* (2016.02); *A61B 17/00234* (2013.01); *A61B 34/30* (2016.02); *F16H 37/12* (2013.01); *A61B 17/28* (2013.01); *A61B 2017/00323* (2013.01); *A61B 2017/00327* (2013.01); *A61B 2017/2916* (2013.01); *A61B 2017/2917* (2013.01); *A61B 2017/2923* (2013.01); *A61B 2017/2931* (2013.01); *A61B 2017/2932* (2013.01); *A61B 2017/2936* (2013.01); *A61B 2017/2937* (2013.01); *A61B 2017/2943* (2013.01); *A61B 2017/2946* (2013.01)

(58) Field of Classification Search
CPC .......... A61B 34/71; A61B 2017/00323; A61B 2090/0818; B25J 19/066; F16H 2007/088; F16H 2025/2065; F16H 2025/2071

USPC .............. 901/21; 74/490.04, 490.11, 490.12
See application file for complete search history.

(56) References Cited

U.S. PATENT DOCUMENTS

| 8,831,782 B2 | 9/2014 | Itkowitz |
| 9,220,569 B2 * | 12/2015 | Parihar .................. A61B 18/12 |
| 2014/0001231 A1 | 1/2014 | Frederick et al. |

(Continued)

FOREIGN PATENT DOCUMENTS

| WO | 2014/151621 | 9/2014 |
| WO | 2014/151952 | 9/2014 |
| WO | 2017155931 A1 | 9/2017 |

OTHER PUBLICATIONS

ISRWO of corresponding PCT/US2018/056404 dated Oct. 12, 2018.

*Primary Examiner* — Bobby Rushing, Jr.
(74) *Attorney, Agent, or Firm* — Vorys, Sater, Seymour and Pease LLP

(57) ABSTRACT

A surgical tool includes a drive housing that houses a plurality of drive cable capstans, an elongate shaft that extends from the drive housing, and an end effector operatively coupled to a distal end of the elongate shaft. A plurality of drive cables extend between the drive housing and the end effector, wherein each drive cable is associated with a corresponding drive cable capstan and rotation of the drive cable capstans correspondingly moves the drive cables to articulate the end effector. A manual release assembly is coupled to the drive housing and includes a release switch that is manually movable between a disengaged position and an engaged position. When the release switch is manually moved to the engaged position, the drive cable capstans are rotated to move the drive cables and thereby manually articulate the end effector.

18 Claims, 13 Drawing Sheets

(51) Int. Cl.
*A61B 17/29* (2006.01)
*A61B 17/28* (2006.01)

(56) References Cited

U.S. PATENT DOCUMENTS

| | | | |
|---|---|---|---|
| 2014/0276761 A1* | 9/2014 | Parihar | A61B 34/30 |
| | | | 606/34 |
| 2014/0276948 A1* | 9/2014 | Zirps | A61F 2/958 |
| | | | 606/130 |
| 2015/0053737 A1* | 2/2015 | Leimbach | A61B 90/03 |
| | | | 227/175.1 |
| 2015/0313676 A1 | 11/2015 | Deodhar | |
| 2016/0287252 A1 | 10/2016 | Parihar | |

* cited by examiner

MANUAL RELEASE ASSEMBLY FOR ROBOTIC SURGICAL TOOL

BACKGROUND

Minimally invasive surgical (MIS) instruments are often preferred over traditional open surgical devices due to reduced post-operative recovery time and minimal scarring. Endoscopic surgery is one type of MIS procedure in which an elongate flexible shaft is introduced into the body of a patient through a natural orifice. Laparoscopic surgery is another type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The trocar also helps facilitate insufflation to elevate the abdominal wall above the organs. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint that creates a more natural hand-like articulation. The instrument's end effector can be articulated (moved) using a cable driven motion system having one or more drive cables that extend through the wrist joint.

A user (e.g., a surgeon) is able to remotely operate an instrument's end effector by grasping and manipulating in space one or more controllers that communicate with a tool driver coupled to the surgical instrument. User inputs are processed by a computer system incorporated into the robotic surgical system and the tool driver responds by actuating the cable driven motion system and, more particularly, the drive cables. Moving the drive cables articulates the end effector to desired positions and configurations.

Various types of end effectors, such as tissue graspers, forceps, needle drivers, and scissors, etc., have opposing jaws designed to open and close for a variety of reasons. In cable driven motion systems, the jaws of such end effectors open and close based on drive cable actuation (movement). In some applications, such end effectors can also incorporate electrocauterizing capabilities to simultaneously cauterize cut tissue.

Since robotic surgical systems operate based on electricity, it may be beneficial to incorporate a failsafe device that can be manually triggered without electrical input. This may prove advantageous, for example, in the event of an electrical disruption that renders the robotic surgical system inoperable. In such a scenario, a failsafe device might allow a user to manually articulate an end effector to safely release and remove the end effector from patient proximity.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to robotic surgical systems and, more particularly, to a failsafe device that allows a user to manually override articulation of an end effector used in robotic surgery.

Embodiments discussed herein describe a failsafe device that can include a manual release assembly incorporated into a surgical tool. The manual release assembly gives a user the ability to manually release an end effector in the event the robotic surgical system becomes inoperable. One example surgical tool includes a drive housing that houses a plurality of drive cable capstans, an elongate shaft that extends from the drive housing, and an end effector operatively coupled to a distal end of the elongate shaft. A plurality of drive cables extend between the drive housing and the end effector, wherein each drive cable is associated with a corresponding drive cable capstan and rotation of the drive cable capstans correspondingly moves the drive cables to articulate the end effector. A manual release assembly is coupled to the drive housing and includes a release switch that is manually movable between a disengaged position and an engaged position. When the release switch is manually moved to the engaged position, the drive cable capstans are rotated to move the drive cables and thereby manually articulate the end effector.

FIGS. 1-5 illustrate the structure and operation of example robotic surgical systems and components thereof.

Figure 1:
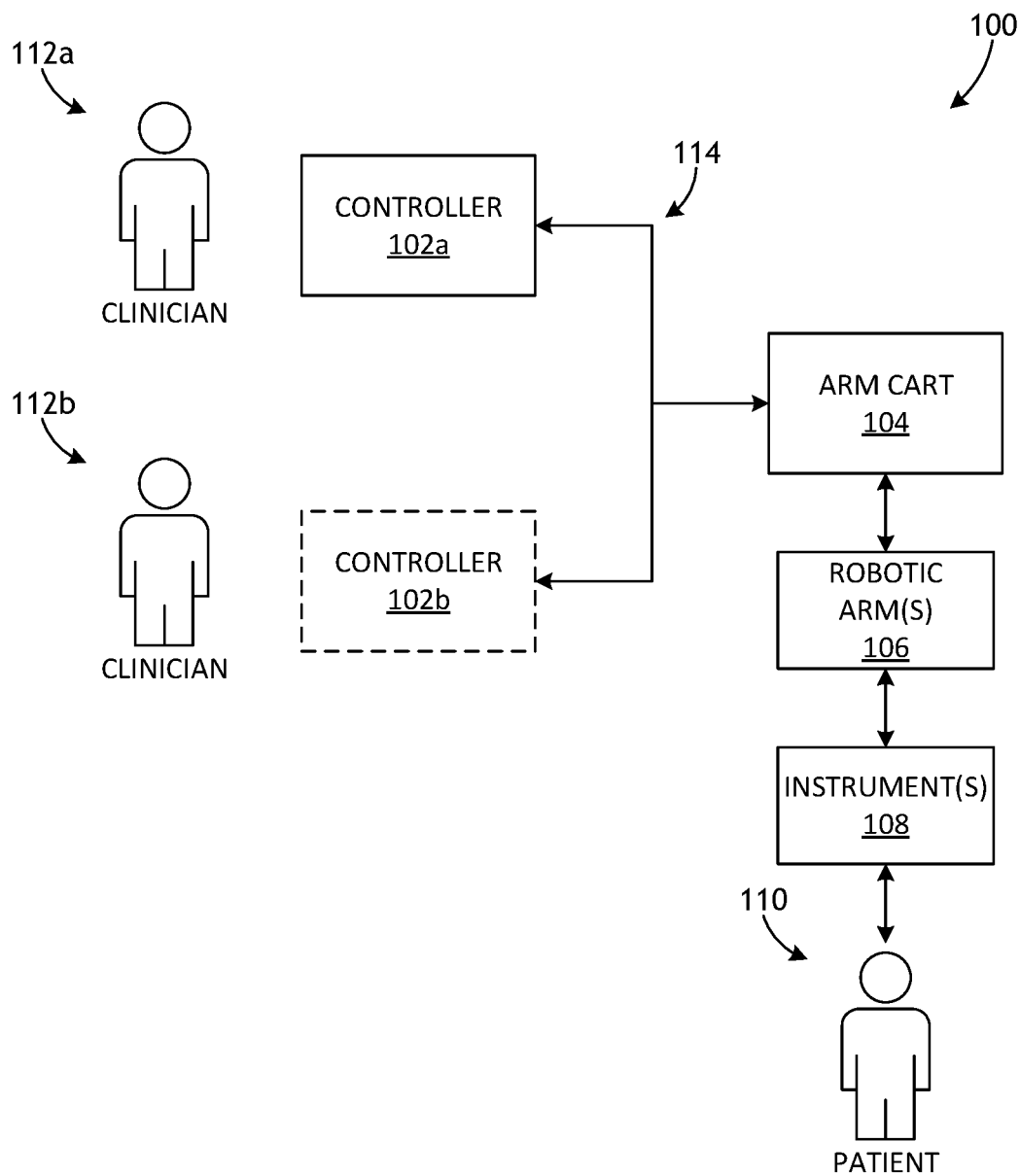
FIG. 1 is a block diagram of an example robotic surgical system 100 that may incorporate some or all of the principles of the present disclosure.

FIG. 1 is a block diagram of an example robotic surgical system 100 that may incorporate some or all of the principles of the present disclosure. As illustrated, the system 100 can include at least one master controller 102a and at least one arm cart 104. The arm cart 104 may be mechanically and/or electrically coupled to one or more robotic arms 106, alternately referred to as "tool drivers". Each robotic arm 106 may include and otherwise mount one or more surgical tools or instruments 108 for performing various surgical tasks on a patient 110. Operation of the arm cart 104, including the arms 106 and instruments 108 may be directed by a clinician 112a (e.g., a surgeon) from the master controller 102a.

In some embodiments, a second master controller 102b (shown in dashed lines) operated by a second clinician 112b may also direct operation of the arm cart 104 in conjunction with the first clinician 112a. In such embodiments, for example, each clinician 102a,b may control different arms 106 of the arm cart 104 or, in some cases, complete control of the arm cart 104 may be passed between the clinicians 102a,b. In some embodiments, additional arm carts (not shown) may be utilized on the patient 110, and these additional arm carts may be controlled by one or more of the master controllers 102a,b.

The arm cart(s) 104 and the master controllers 102a,b may be in communication with one another via a communications link 114, which may be any type of wired or wireless communications link configured to carry suitable types of signals (e.g., electrical, optical, infrared, etc.) according to any communications protocol. The communications link 114 may be an actual physical link or it may be a logical link that uses one or more actual physical links. When the link is a logical link the type of physical link may be a data link, uplink, downlink, fiber optic link, point-to-point link, for example, as is well known in the computer networking art to refer to the communications facilities that connect nodes of a network. Example implementations of robotic surgical systems, such as the system 100, are disclosed in U.S. Pat. No. 7,524,320, the contents of which are incorporated herein by reference. The various particularities of such devices will not be described in detail herein beyond that which may be necessary to understand various embodiments and forms of the various embodiments of robotic surgery apparatus, systems, and methods disclosed herein.

Figure 2:
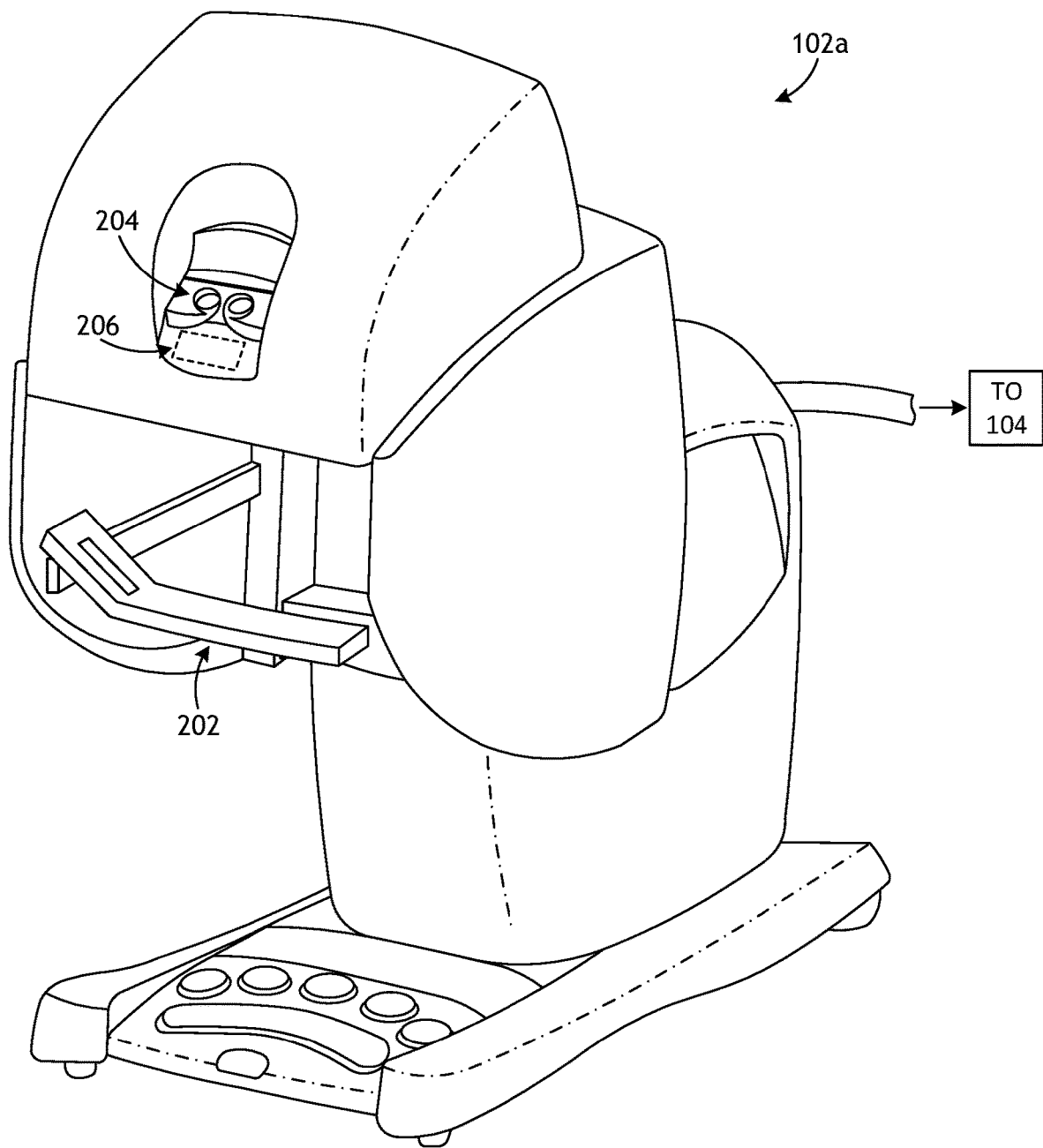
FIG. 2 is an isometric view of an example master controller that may be used to operate a robotic arm slave cart.

FIG. 2 is an example embodiment of the master controller 102a that may be used to operate a robotic arm slave cart, such as the arm cart 104 of FIG. 1. The master controller 102a and its associated arm cart 104, as well as their respective components and control systems, are collectively referred to herein as a "robotic surgical system." Examples of such systems and devices are disclosed in U.S. Pat. No. 7,524,320 and, therefore, will not be described in detail herein beyond that which may be necessary to understand various embodiments and forms of the present invention.

The master controller 102a generally includes one or more controllers 202 that can be grasped by a surgeon (e.g., the clinician 112a of FIG. 1) and manipulated in space while the surgeon views the procedure via a stereo display 204. The master controllers 202 generally comprise manual input devices designed to move in multiple degrees of freedom, and which often further have an actuatable handle for actuating a surgical instrument (e.g., the surgical instrument(s) 108 of FIG. 1), for example, for opening and closing opposing jaws, applying an electrical potential to an electrode, or the like.

In the illustrated example, the master controller 102a further includes an optional feedback meter 206 viewable by the surgeon via the display 204 to provide the surgeon with a visual indication of the amount of force being applied to the surgical instrument (i.e., a cutting instrument or dynamic clamping member). Other sensor arrangements may be employed to provide the master controller 102a with an indication of other surgical instrument metrics, such as whether a staple cartridge has been loaded into an end effector or whether an anvil has been moved to a closed position prior to firing, for example.

Figure 3:
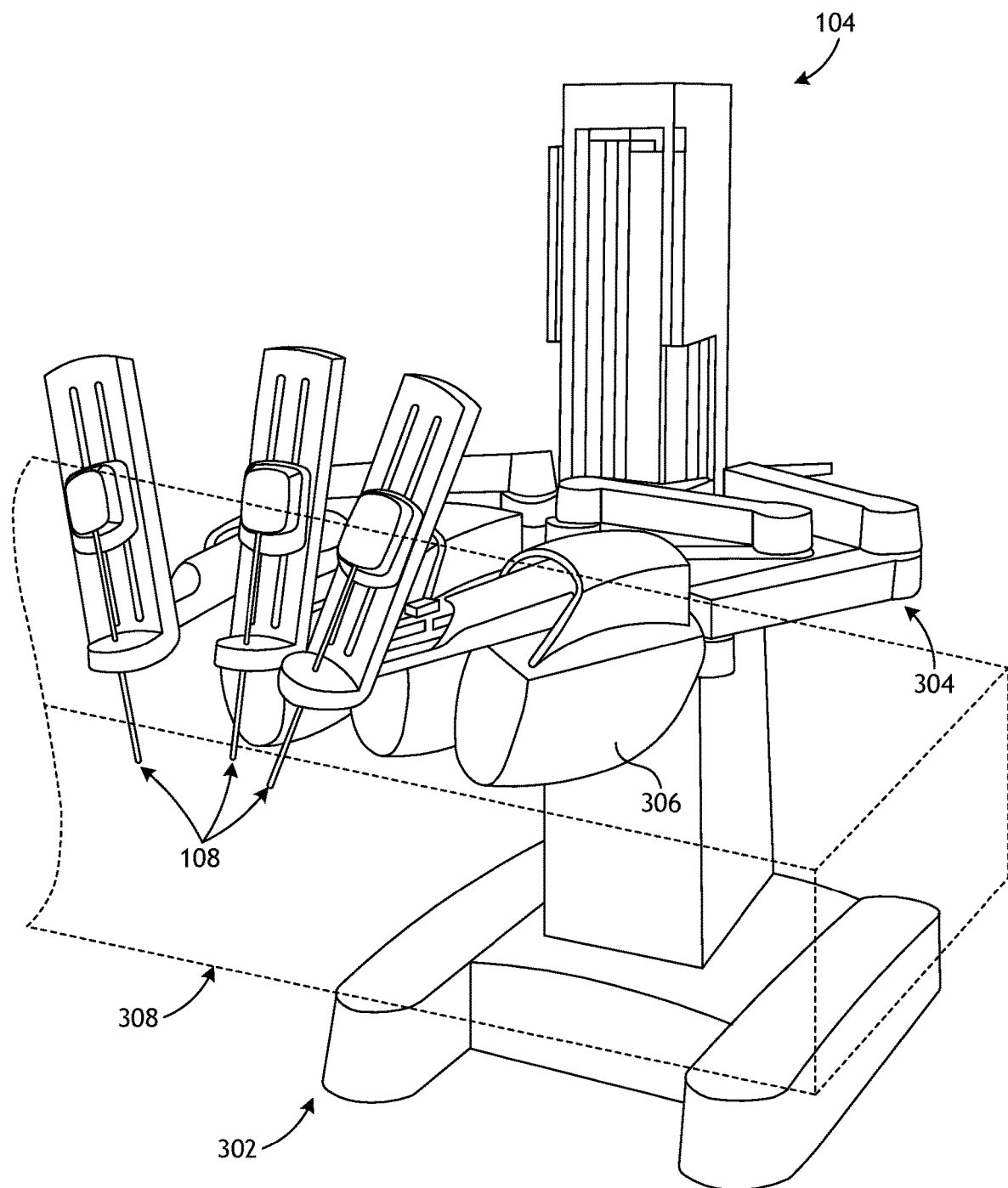
FIG. 3 is an isometric view of an example robotic arm cart used to actuate a plurality of surgical instruments.

FIG. 3 depicts an example embodiment of the robotic arm cart 104 used to actuate a plurality of surgical instruments 108, alternately referred to as "surgical tools." Various robotic surgery systems and methods employing master controller and robotic arm cart arrangements are described in U.S. Pat. No. 6,132,368, the contents of which are hereby incorporated by reference. As illustrated, the robotic arm cart 104 may include a base 302 that supports three surgical instruments 108, and the surgical instruments 108 are each supported by a series of manually articulatable linkages, generally referred to as set-up joints 304, and a robotic manipulator 306. These structures are herein illustrated with protective covers extending over much of the robotic linkage. These protective covers may be optional, and may be limited in size or entirely eliminated in some embodiments, for example, to minimize the inertia that is encountered by the servo mechanisms used to manipulate such devices, to limit the volume of moving components so as to avoid collisions, and/or to limit the overall weight of the cart 104.

The cart 104 will generally have dimensions suitable for transporting the cart 104 between operating rooms. The cart 104 may be configured to typically fit through standard operating room doors and onto standard hospital elevators. In some embodiments, the cart 104 may include a wheel system (or other transportation system) that allows the cart 104 to be positioned adjacent an operating table by a single attendant. In various embodiments, an automated reloading system including a base portion may be strategically located within a work envelope 308 of the robotic arm cart 104.

Figure 4:
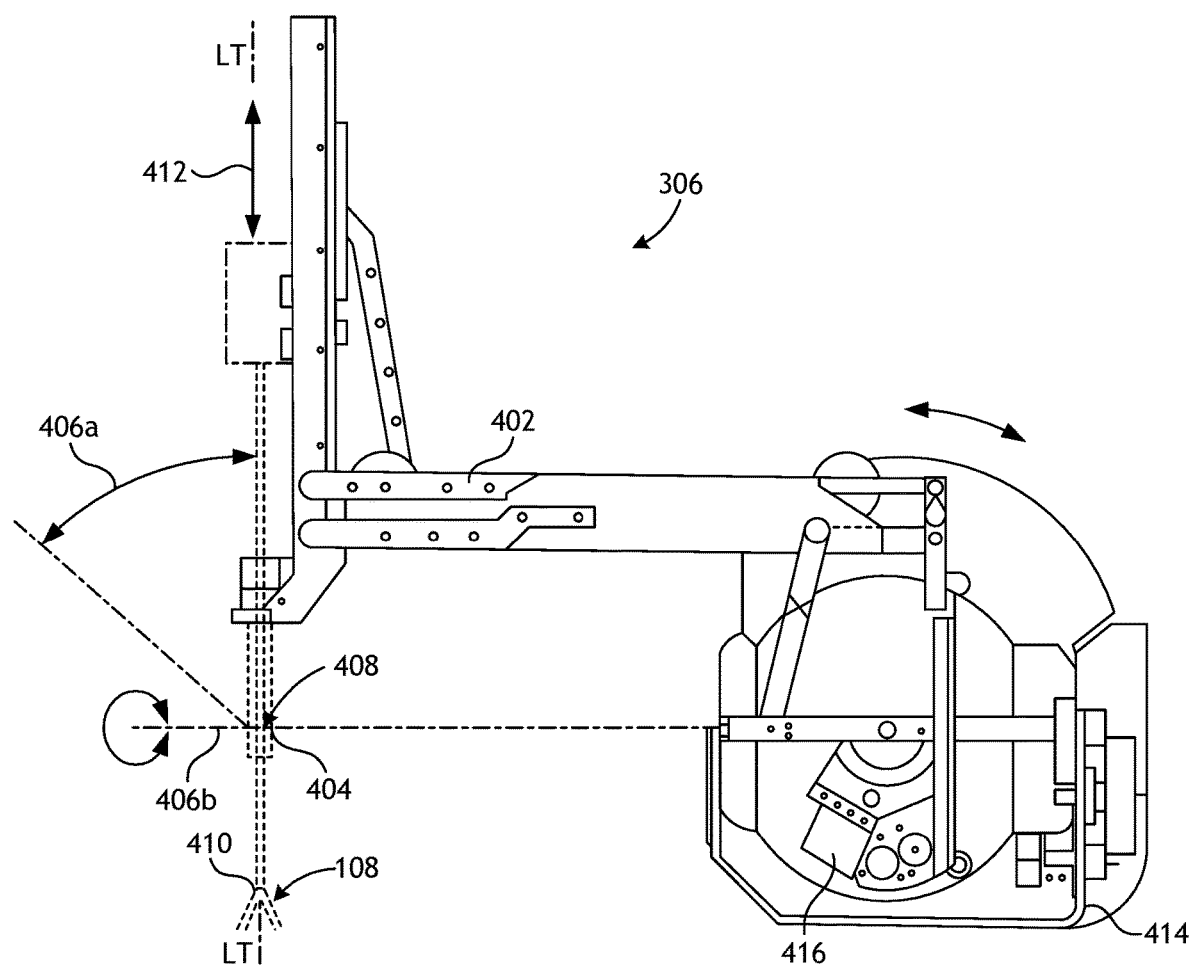
FIG. 4 is a side view schematic diagram of an example robotic tool driver including linkage to constrain movement of a surgical tool.

FIG. 4 is a side view schematic diagram of an example embodiment of the robotic manipulator 306. As illustrated, the robotic manipulator 306 may include a linkage 402 that constrains movement of the surgical instrument 108 coupled thereto. The linkage 402 includes rigid links coupled by rotational joints in a parallelogram arrangement so that the surgical instrument 108 rotates around a point 404 in space.

The parallelogram arrangement constrains rotation to pivoting about a "pitch axis" that extends axis through the point 404, as indicated by a pitch arrow 406a. The links supporting the parallelogram linkage 402 are pivotally mounted to set-up joints 304 (FIG. 3) so that the surgical instrument 108 further rotates about a second axis 406b, referred to as the "yaw axis." The pitch axis and the yaw axis 406b intersect at a remote center 408, which is aligned along a shaft 410 of the surgical instrument 108.

The surgical instrument 108 may have further degrees of driven freedom as supported by the robotic manipulator 306, including sliding motion of the surgical instrument 108 along a longitudinal tool axis "LT-LT". As the surgical instrument 108 slides (translates) along the longitudinal tool axis LT-LT relative to the robotic manipulator 306 (arrow 412), the remote center 408 remains fixed relative to a base 414 of the robotic manipulator 306. Hence, the entire robotic manipulator 306 is generally moved to re-position the remote center 408.

The linkage 402 of the robotic manipulator 306 is driven by a series of motors 416. These motors 416 actively move the linkage 402 in response to commands from a processor of a control system. The motors 416 may also be employed to manipulate the surgical instrument 108.

Figure 5:
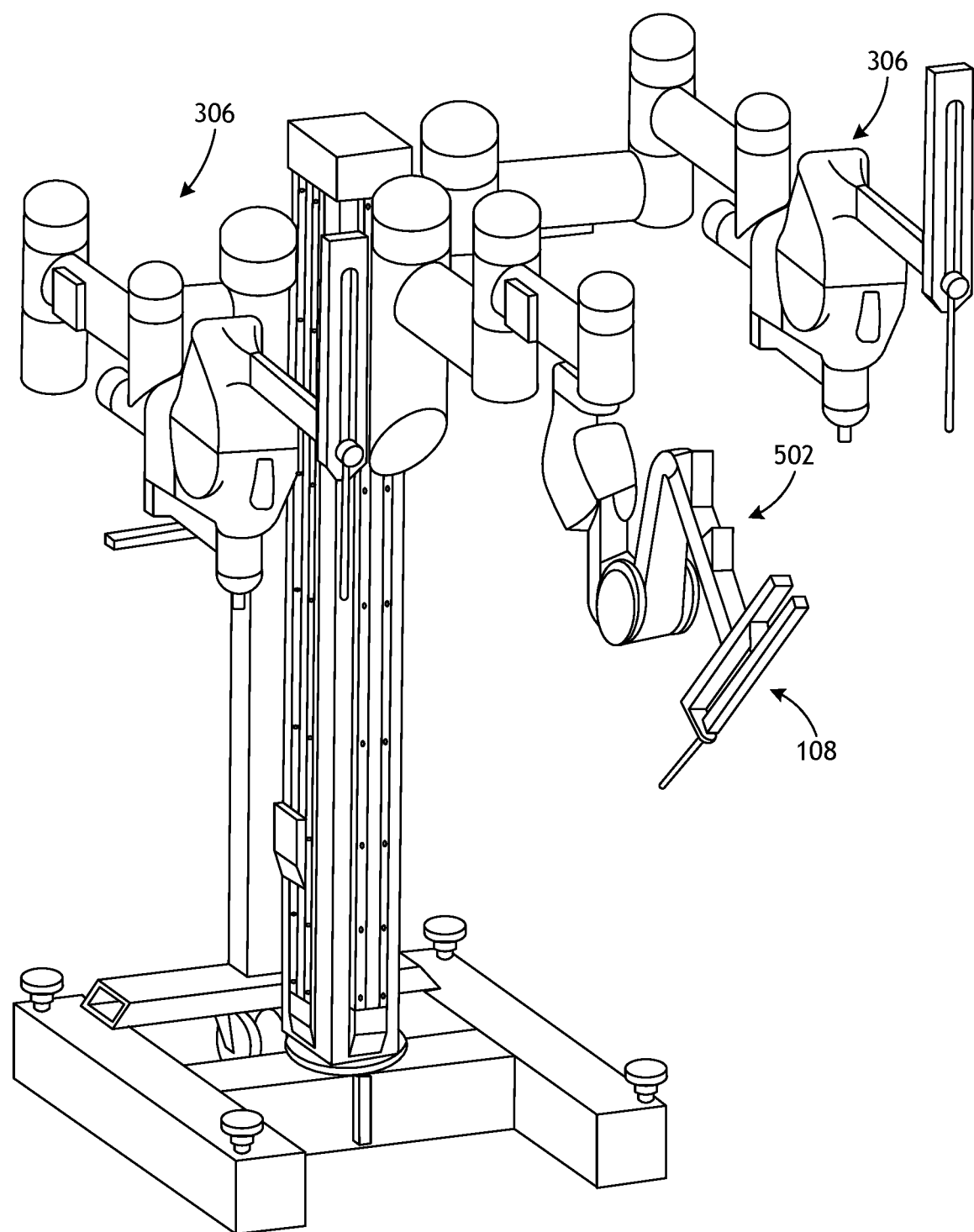
FIG. 5 is a perspective view of an alternative example robotic tool driver.

FIG. 5 is a perspective view of an alternative example robotic manipulator 502, used in conjunction with two robotic manipulators similar to the robotic manipulators 306 described in FIG. 4. As illustrated, a surgical instrument 108 is supported by the robotic manipulator 502 between the two robotic manipulators 306 generally described above. Those of ordinary skill in the art will appreciate that various embodiments of the present invention may incorporate a wide variety of alternative robotic structures, including those described in U.S. Pat. No. 5,878,193, the contents of which are hereby incorporated by reference. Additionally, while the data communication between a robotic component and the processor of the robotic surgical system is primarily described herein with reference to communication between the surgical instrument 108 and the master controller 102*a* (FIG. 2), it should be understood that similar communication may take place between circuitry of a robotic manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like.

Figure 6:
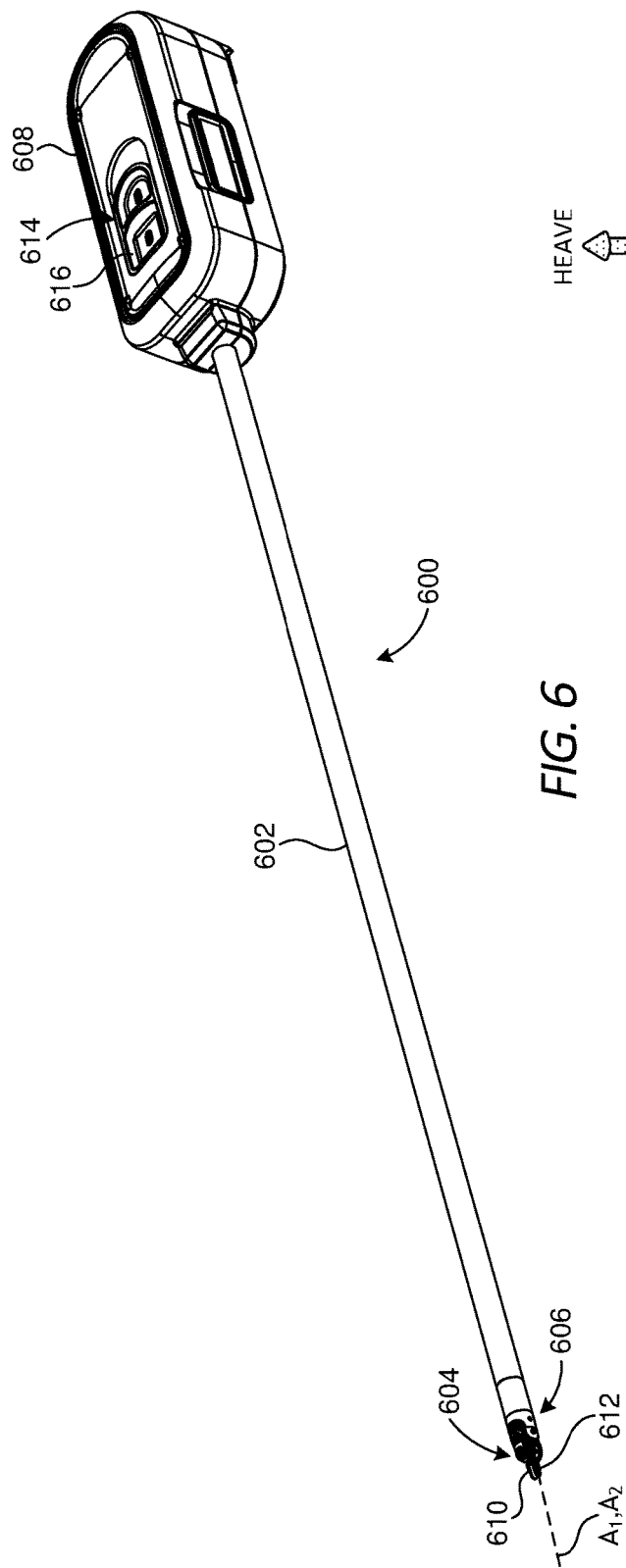
FIG. 6 is a side view of an example surgical tool that may incorporate some or all of the principles of the present disclosure.

FIG. 6 is side view of an example surgical tool 600 that may incorporate some or all of the principles of the present disclosure. The surgical tool 600 may be the same as or similar to the surgical instrument(s) 108 of FIGS. 1 and 3-5) and, therefore, may be used in conjunction with a robotic surgical system, such as the robotic surgical system 100 of FIG. 1. Accordingly, the surgical tool 600 may be designed to be releasably coupled to a tool driver included in the robotic surgical system 100.

As illustrated, the surgical tool 600 includes an elongate shaft 602, an end effector 604, a wrist 606 (alternately referred to as a "wrist joint") that couples the end effector 604 to the distal end of the shaft 602, and a drive housing 608 coupled to the proximal end of the shaft 602. In applications where the surgical tool is used in conjunction with a robotic surgical system (e.g., the robotic surgical system 100 of FIG. 1), the drive housing 608 can include coupling features that releasably couple the surgical tool 600 to the robotic surgical system.

The terms "proximal" and "distal" are defined herein relative to a robotic surgical system having an interface configured to mechanically and electrically couple the surgical tool 600 (e.g., at the housing 608) to a robotic manipulator. The term "proximal" refers to the position of an element closer to the robotic manipulator and the term "distal" refers to the position of an element closer to the end effector 604 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 600, the end effector 604 is configured to move (pivot) relative to the shaft 602 at the wrist 606 to position the end effector 604 at desired orientations and locations relative to a surgical site (not illustrated). The housing 608 includes (contains) various mechanisms designed to control operation of various features associated with the end effector 604 (e.g., clamping, firing, rotation, articulation, energy delivery, etc.). In at least some embodiments, the shaft 602, and hence the end effector 604 coupled thereto, is configured to rotate about a longitudinal axis $A_1$ of the shaft 602. In such embodiments, at least one of the mechanisms included (housed) in the housing 608 is configured to control rotational movement of the shaft 602 about the longitudinal axis $A_1$.

The surgical tool 600 can have any of a variety of configurations capable of performing at least one surgical function. For example, the surgical tool 600 may include, but is not limited to, forceps, a grasper, a needle driver, scissors, an electro cautery tool, a stapler, a clip applier, a suction tool, an irrigation tool, an imaging device (e.g., an endoscope or ultrasonic probe), or any combination thereof. In some embodiments, the surgical tool 600 may be configured to apply energy to tissue, such as radiofrequency (RF) energy.

The shaft 602 is an elongate member extending distally from the housing 608 and has at least one lumen extending therethrough along its axial length. In some embodiments, the shaft 602 may be fixed to the housing 608, but could alternatively be rotatably mounted to the housing 608 to allow the shaft 602 to rotate about the longitudinal axis $A_1$. In yet other embodiments, the shaft 602 may be releasably coupled to the housing 608, which may allow a single housing 608 to be adaptable to various shafts having different end effectors.

The end effector 604 can have a variety of sizes, shapes, and configurations. In the illustrated embodiment, the end effector 604 includes opposing jaws 610, 612 configured to move (articulate) between open and closed positions. Accordingly, the end effector 604 can comprise, but is not limited to, a tissue grasper, a clip applier, scissors, a needle driver, a babcock including a pair of opposed grasping jaws, etc. One or both of the jaws 610, 612 may be configured to pivot at the wrist 606 to articulate the end effector 604 between the open and closed positions.

Figure 7:
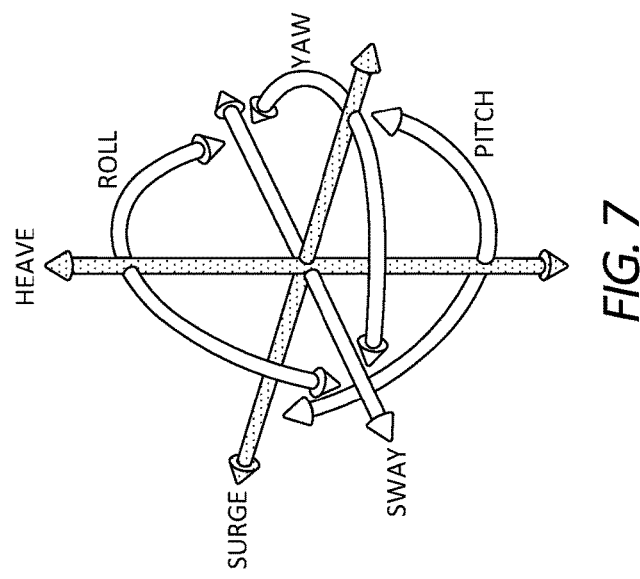
FIG. 7 illustrates potential degrees of freedom in which the wrist of FIG. 1 may be able to articulate (pivot).

FIG. 7 illustrates the potential degrees of freedom in which the wrist 606 may be able to articulate (pivot). The wrist 606 can have any of a variety of configurations. In general, the wrist 606 comprises a joint configured to allow pivoting movement of the end effector 604 relative to the shaft 602. The degrees of freedom of the wrist 606 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 604) with respect to a given Cartesian coordinate frame of reference. As depicted in FIG. 7, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 606 (e.g., X-axis), yaw movement about a second axis of the wrist 606 (e.g., Y-axis), and combinations thereof to allow for 360° rotational movement of the end effector 604 about the wrist 606. In other applications, the pivoting motion can be limited to movement in a single plane, e.g., only pitch movement about the first axis of the wrist 606 or only yaw movement about the second axis of the wrist 606, such that the end effector 604 moves only in a single plane. In addition, the wrist 606 may include a roll movement about a third axis of the wrist (e.g., Z-axis), whereby the wrist 606 rotates about and relative to the shaft 602.

Referring again to FIG. 6, the surgical tool 600 includes a plurality of drive cables (obscured in FIG. 6) that form part of a cable driven motion system configured to facilitate movement of (articulate) the end effector 604 relative to the shaft 602. Moving the drive cables moves the end effector 604 between an unarticulated position and an articulated position. The end effector 604 is depicted in FIG. 6 in the unarticulated position where a longitudinal axis $A_2$ of the end effector 604 is substantially aligned with the longitudinal axis $A_1$ of the shaft 602, such that the end effector 604 is at a substantially zero angle relative to the shaft 602. Due to factors such as manufacturing tolerance and precision of measurement devices, the end effector 604 may not be at a precise zero angle relative to the shaft 602 in the unarticulated position, but may nevertheless be considered "substantially aligned" thereto. In the articulated position, the longitudinal axes $A_1$, $A_2$ would be angularly offset from each other such that the end effector 604 is at a non-zero angle relative to the shaft 602.

According to embodiments of the present disclosure, the surgical tool 600 may further include a manual release assembly 614 that may be manually actuated by a user (e.g., a surgeon) to override the cable driven system and thereby manually articulate the end effector 604. For the illustrated embodiment, employing the manual release assembly 614 would result in the jaws 610, 612 opening, which might prove beneficial for a variety of reasons. In some applications, for example, the manual release assembly 614 may be employed in the event of an electrical disruption that renders the surgical tool 600 inoperable. In such applications, the user would be able to manually open the jaws 610, 612 and thereby release any grasped tissue and remove the surgical tool 600. In other applications, the manual release assembly 614 may be actuated (enabled) to open the jaws 610, 612 in preparation for cleaning and/or sterilization of the surgical tool 600.

In the illustrated embodiment, the manual release assembly 614 includes a release switch 616 movably positioned on the drive housing 608. A user is able to manually move (slide) the release switch 616 from a disengaged position, as shown, to an engaged position. In the disengaged position, the surgical tool 600 is able to operate as normal. As the release switch 616 moves to the engaged position, however, various internal component parts of the manual release assembly 614 housed within the drive housing 608 are simultaneously moved, thereby resulting in articulation of the end effector 604.

It should be noted that while the release switch 616 is depicted in FIG. 6 as being accessible via a top surface of the drive housing 608, the illustrated position of the release switch 616 is just one example and should not be considered limiting to the scope of the present disclosure. Moreover, the release switch 616 is just one example of a means to manually enable (actuate) the manual release assembly 614 and, therefore, should not be considered limiting to the scope of the present disclosure.

Figure 8:
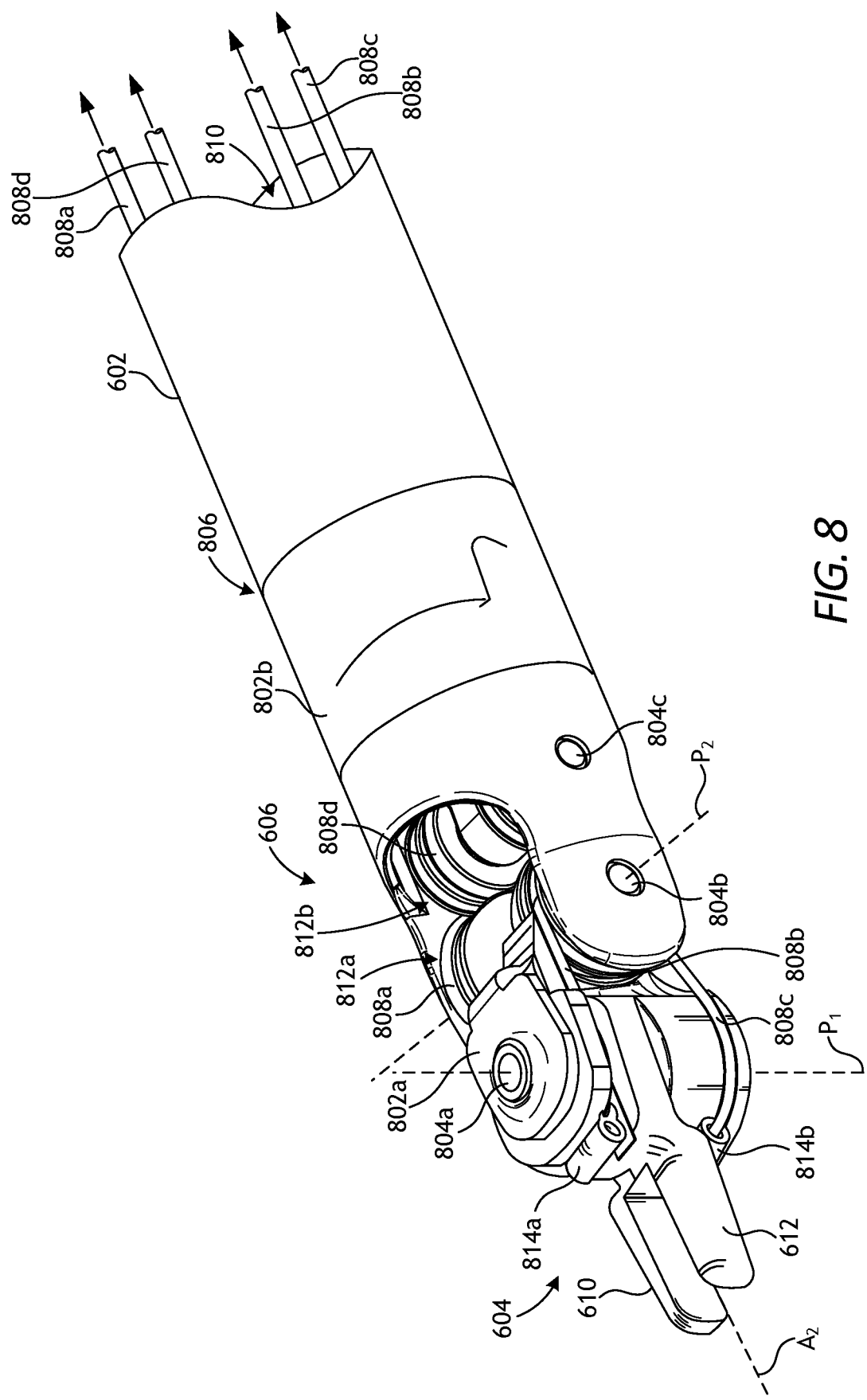
FIG. 8 is an enlarged isometric view of the distal end of the surgical tool of FIG. 1.

FIG. 8 is an enlarged isometric view of the distal end of the surgical tool 600 of FIG. 6. More specifically, FIG. 8 depicts enlarged views of the end effector 604 and the wrist 606, with the end effector 604 in the unarticulated position where the jaws 610, 612 are closed. The wrist 606 operatively couples the end effector 604 to the shaft 602. To accomplish this, the wrist 606 includes a distal clevis 802a and a proximal clevis 802b. The end effector 604 (i.e., the jaws 610, 612) is rotatably mounted to the distal clevis 802a at a first axle 804a, the distal clevis 802a is rotatably mounted to the proximal clevis 802b at a second axle 804b, and the proximal clevis 802b is coupled to a distal end 806 of the shaft 602.

The wrist 606 provides a first pivot axis $P_1$ that extends through the first axle 804a and a second pivot axis $P_2$ that extends through the second axle 804b. The first pivot axis $P_1$ is substantially perpendicular (orthogonal) to the longitudinal axis $A_2$ of the end effector 604, and the second pivot axis $P_2$ is substantially perpendicular (orthogonal) to both the longitudinal axis $A_2$ and the first pivot axis $P_1$. Movement about the first pivot axis $P_1$ provides "yaw" articulation of the end effector 604, and movement about the second pivot axis $P_2$ provides "pitch" articulation of the end effector 604. In the illustrated embodiment, the jaws 610, 612 are mounted at the first pivot axis $P_1$, thereby allowing the jaws 610, 612 to pivot relative to each other to open and close the end effector 604 or alternatively pivot in tandem to articulate the orientation of the end effector 604.

A plurality of drive cables 808, shown as drive cables 808a, 808b, 808c, and 808d, extend longitudinally within a lumen 810 defined by the shaft 602 and pass through the wrist 606 to be operatively coupled to the end effector 604. The drive cables 808a-d form part of the cable driven motion system briefly described above, and may be referred to and otherwise characterized as cables, bands, lines, cords, wires, ropes, strings, twisted strings, elongate members, etc. The drive cables 808a-d can be made from a variety of materials including, but not limited to, metal (e.g., tungsten, stainless steel, etc.) or a polymer. Example drive cables are described in U.S. Patent Pub. No. 2015/0209965 entitled "Compact Robotic Wrist," and U.S. Patent Pub. No. 2015/0025549 entitled "Hyperdexterous Surgical System," the contents of which are hereby incorporated by reference. The lumen 810 can be a single lumen, as illustrated, or can alternatively comprise a plurality of independent lumens that each receive one or more of the drive cables 808a-d.

The drive cables 808a-d extend proximally from the end effector 604 to the drive housing 608 (FIG. 6) where they are operatively coupled to various actuation mechanisms or devices housed (contained) therein to facilitate longitudinal movement (translation) of the drive cables 808a-d within the lumen 810. Selective actuation of all or a portion of the drive cables 808a-d causes the end effector 604 (e.g., one or both of the jaws 610, 612) to articulate (pivot) relative to the shaft 602. More specifically, selective actuation causes a corresponding drive cable 808a-d to translate longitudinally within the lumen of the shaft 602 and thereby cause pivoting movement of the end effector 604. One or more drive cables 808a-d, for example, may translate longitudinally to cause the end effector 604 to articulate (e.g., both of the jaws 610, 612 angled in a same direction), to cause the end effector 604 to open (e.g., one or both of the jaws 610, 612 move away from the other), or to cause the end effector 604 to close (e.g., one or both of the jaws 610, 612 move toward the other).

Moving the drive cables 808a-d can be accomplished in a variety of ways, such as by triggering an associated actuator or mechanism operatively coupled to or housed within the drive housing 608 (FIG. 6). Moving a given drive cable 808a-d constitutes applying tension (i.e., pull force) to the given drive cable 808a-d in a proximal direction, which causes the given drive cable 808a-d to translate and thereby cause the end effector 604 to move (articulate) relative to the shaft 602.

The wrist 606 includes a first plurality of pulleys 812a and a second plurality of pulleys 812b, each configured to interact with and redirect the drive cables 808a-d for engagement with the end effector 604. The first plurality of pulleys 812a is mounted to the proximal clevis 802b at the second axle 804b and the second plurality of pulleys 812b is also mounted to the proximal clevis 802b but at a third axle 804c located proximal to the second axle 804b. The first and second pluralities of pulleys 812a,b cooperatively redirect the drive cables 808a-d through an "S" shaped pathway before the drive cables 808a-d are operatively coupled to the end effector 604.

In at least one embodiment, one pair of drive cables 808a-d is operatively coupled to each jaw 610, 612 and configured to "antagonistically" operate the corresponding jaw 610, 612. In the illustrated embodiment, for example, a first connector 814a mounted to the first jaw 610 couples the first and second drive cables 808a,b, and a second connector 814b mounted to the second jaw 612 couples the third and fourth drive cables 808c,d. Actuation of the first drive cable 808a acts on the first connector 814a and thereby pivots the first jaw 610 about the first pivot axis $P_1$ toward the open position. In contrast, actuation of the second drive cable 808b also acts on the first connector 814a but pivots the first jaw 610 about the first pivot axis $P_1$ in the opposite direction and toward the closed position. Similarly, actuation of the third drive cable 808c acts on the second connector 814b and thereby pivots the second jaw 612 about the first pivot axis $P_1$ toward the open position, while actuation of the fourth drive cable 808d also acts on the second connector 814ab but pivots the second jaw 612 about the first pivot axis $P_1$ in the opposite direction and toward the closed position.

Accordingly, the drive cables 808a-d may be characterized or otherwise referred to as "antagonistic" cables that cooperatively (yet antagonistically) operate to cause relative or tandem movement of the first and second jaws 610, 612. When the first drive cable 808a is actuated (moved), the second drive cable 808b naturally follows as coupled to the first drive cable 808a at the first connector 814a, and vice versa. Similarly, when the third drive cable 808c is actuated, the fourth drive cable 808d naturally follows as coupled to the third drive cable 808c at the second connector 814b, and vice versa.

Figure 9:
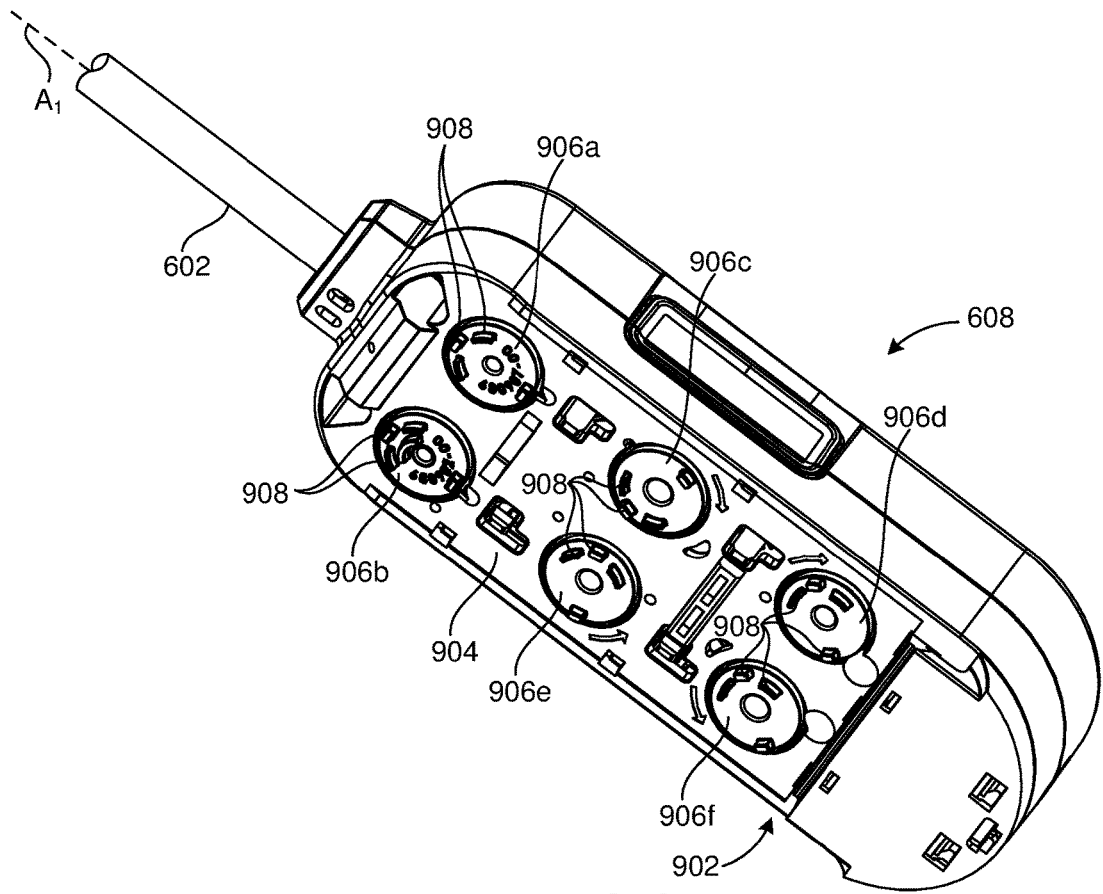
FIG. 9 is an isometric bottom view of the drive housing of the surgical tool of FIG. 6.

FIG. 9 is a bottom view of the drive housing 608, according to one or more embodiments. As illustrated, the drive housing 608 (alternately referred to as a "puck") may include a tool mounting portion 902 used to operatively couple the drive housing 608 to a tool driver of a robotic manipulator (e.g., the robotic manipulators 306, 502 of FIGS. 3 and 5, respectively). The tool mounting portion 902 may releasably couple the drive housing 608 to a tool driver in a variety of ways, such as by clamping thereto, clipping thereto, or slidably mating therewith. In some embodiments, the tool mounting portion 902 may include an array of electrical connecting pins, which may be coupled to an electrical connection on the mounting surface of the tool driver. While the tool mounting portion 902 is described herein with reference to mechanical, electrical, and magnetic coupling elements, it should be understood that a wide variety of telemetry modalities might be used, including infrared, inductive coupling, or the like.

The tool mounting portion 902 includes and otherwise provides an interface 904 configured to mechanically, magnetically, and/or electrically couple the drive housing 608 to the tool driver. As illustrated, the interface 904 includes and supports a plurality of inputs, shown as inputs 906a, 906b, 906c, 906d, 906e, and 906f. In at least one embodiment, each input 906a-f comprises a rotatable disc configured to align with and couple to a corresponding actuator of a given tool driver. Moreover, each input 906a-f provides or defines one or more surface features 908 configured to align with mating surface features provided on the corresponding actuator. The surface features 908 can include, for example, various protrusions and/or indentations that facilitate a mating engagement. In some embodiments, some or all of the inputs 906a-f may include one surface feature 908 that is positioned closer to an axis of rotation of the associated input 906a-f than the other surface feature(s) 908. This may help to ensure positive angular alignment of each input 906a-f.

In some embodiments, actuation of the first input 906a may be configured to control rotation of the elongate shaft 602 about its longitudinal axis $A_1$. The elongate shaft 602 may be rotated clockwise or counter-clockwise depending on the rotational actuation of the first input 906a. In some embodiments, actuation of the second input 906b may be configured to control a lockout mechanism (alternately referred to as a deadbolt), which locks the end effector 604 (FIGS. 6 and 8) in a predetermined pose or position. In some embodiments, actuation of the third input 906c, the fourth input 906d, the fifth input 906e, and the sixth input 906f may be configured to operate movement (axial translation) of the drive cables 808a-d (FIG. 8), which results in the articulation of the end effector 604. Each of the inputs 906a-f may be actuated based on user inputs communicated to a tool driver coupled to the interface 904, and the user inputs may be received via a computer system incorporated into the robotic surgical system.

Figure 10:
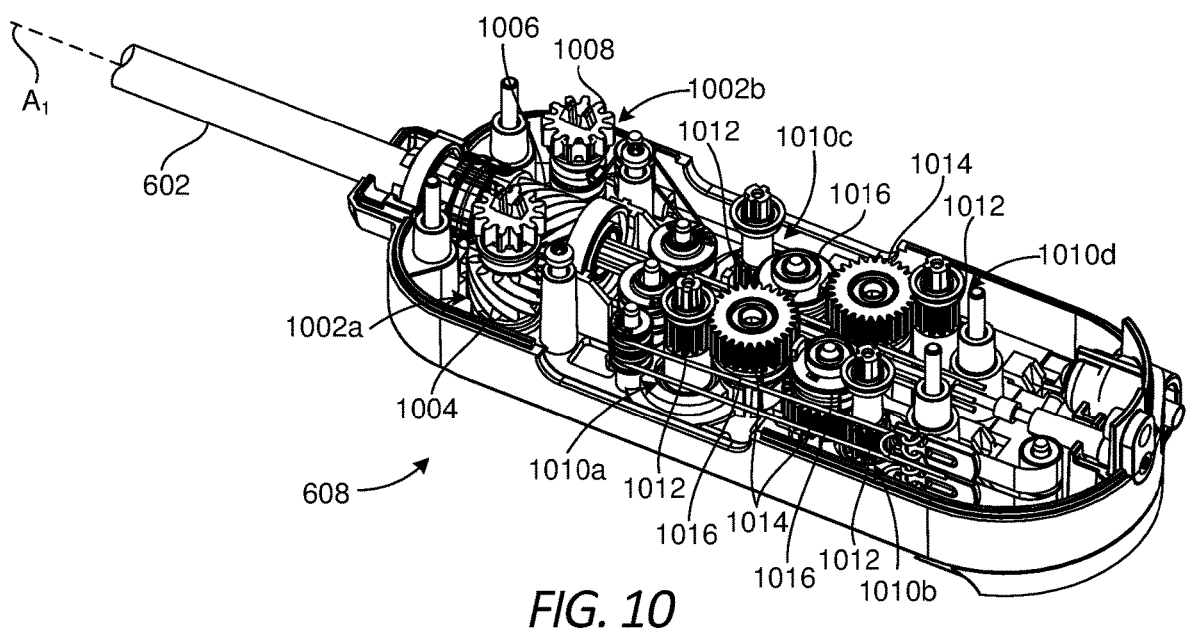
FIG. 10 is an isometric exposed view of the interior of the drive housing of the surgical tool of FIG. 6.

FIG. 10 is an isometric exposed view of the interior of the drive housing 608, according to one or more embodiments. Several component parts that may be otherwise contained within the drive housing 608 are not shown in FIG. 10 to enable discussion of the depicted component parts. As illustrated, a first capstan 1002a and a second capstan 1002b are contained (housed) within the drive housing 608. The first capstan 1002a may be operatively coupled to or extend from the first input 906a (FIG. 9), and the second capstan 1002b may be operatively coupled to or extend from the second input 906b (FIG. 9). Accordingly, actuation of the first input 906a results in rotation of the first capstan 1002a and actuation of the second input 906b results in rotation of the second capstan 1002b.

A spiral worm drive gear 1004 is coupled to or forms part of the first capstan 1002a. The spiral worm drive gear 1004 may be configured to mesh and interact with a driven gear 1006 secured within the drive housing 608 and operatively coupled to the shaft 602 such that rotation of the driven gear 1006 correspondingly rotates the shaft 602. Accordingly, rotation of the spiral worm drive gear 1004 (via actuation of the first input 906a of FIG. 9) will drive the driven gear 1006 and thereby control rotation of the elongate shaft 602 about the longitudinal axis $A_1$.

A pinion gear 1008 may be coupled to the second capstan 1002b and configured to mesh and interact with a rack gear (not shown) contained within the drive housing 608. The rack gear may be operatively coupled to a lockout mechanism (not shown) that is movable to lock the end effector 604 (FIGS. 6 and 8) in a predetermined pose or position. Accordingly, rotation of the pinion gear 1008 (via actuation of the second input 906b of FIG. 9) will control the lockout mechanism and thereby lock and unlock the end effector 604 when desired.

The drive housing 608 further contains or houses a first drive cable capstan 1010a, a second drive cable capstan 1010*b*, a third drive cable capstan 1010*c*, and a fourth drive cable capstan 1010*d*. While four drive cable capstans 1010*a-d* are depicted in FIG. 10, alternative embodiments may include more or less than four, without departing from the scope of the disclosure. In the illustrated embodiment, the first drive cable capstan 1010*a* is operatively coupled to or extends from the third input 906*c* (FIG. 9), the second drive cable capstan 1010*b* is operatively coupled to or extends from the fourth input 906*d* (FIG. 9), the third drive cable capstan 1010*c* is operatively coupled to or extends from the fifth input 906*e* (FIG. 9), and the fourth drive cable capstan 1010*d* is operatively coupled to or extends from the sixth input 906*f* (FIG. 9). Accordingly, actuation of the third input 906*c* results in rotation of the first drive cable capstan 1010*a*, actuation of the fourth input 906*d* results in rotation of the second drive cable capstan 1010*b*, actuation of the fifth input 906*e* results in rotation of the third drive cable capstan 1010*c*, and actuation of the sixth input 906*f* results in rotation of the fourth drive cable capstan 1010*d*.

As illustrated, a corresponding drive gear 1012 is coupled to or forms part of each drive cable capstan 1010*a-d*. Moreover, each drive gear 1012 is positioned to mesh and interact with a corresponding driven gear 1014 (three shown, and one obscured) rotatably mounted within the drive housing 608. Each driven gear 1012 includes or is otherwise coupled to a corresponding cable pulley 1016 (three shown, and one obscured). Each cable pulley 1016 is configured to be operatively coupled to (e.g., has wrapped there around) a corresponding one of the drive cables 808*a-d* (FIG. 8), which are not shown in FIG. 10. Accordingly, rotation of the first drive cable capstan 1010*a* (via actuation of the third input 906*c* of FIG. 9) will correspondingly rotate the associated drive gear 1012 and drive the associated driven gear 1014, which controls movement of the first drive cable 808*a* (FIG. 8); rotation of the second drive cable capstan 1010*b* (via actuation of the fourth input 906*d* of FIG. 9) will correspondingly rotate the associated drive gear 1012 and drive the associated driven gear 1014, which controls movement of the second drive cable 808*b* (FIG. 8); rotation of the third drive cable capstan 1010*c* (via actuation of the fifth input 906*e* of FIG. 9) will correspondingly rotate the associated drive gear 1012 and drive the associated driven gear 1014, which controls movement of the third drive cable 808*c* (FIG. 8); and rotation of the fourth drive cable capstan 1010*d* (via actuation of the sixth input 906*f* of FIG. 9) will correspondingly rotate the associated drive gear 1012 and drive the associated driven gear 1014, which controls movement of the fourth drive cable 808*d* (FIG. 8).

Figure 11:
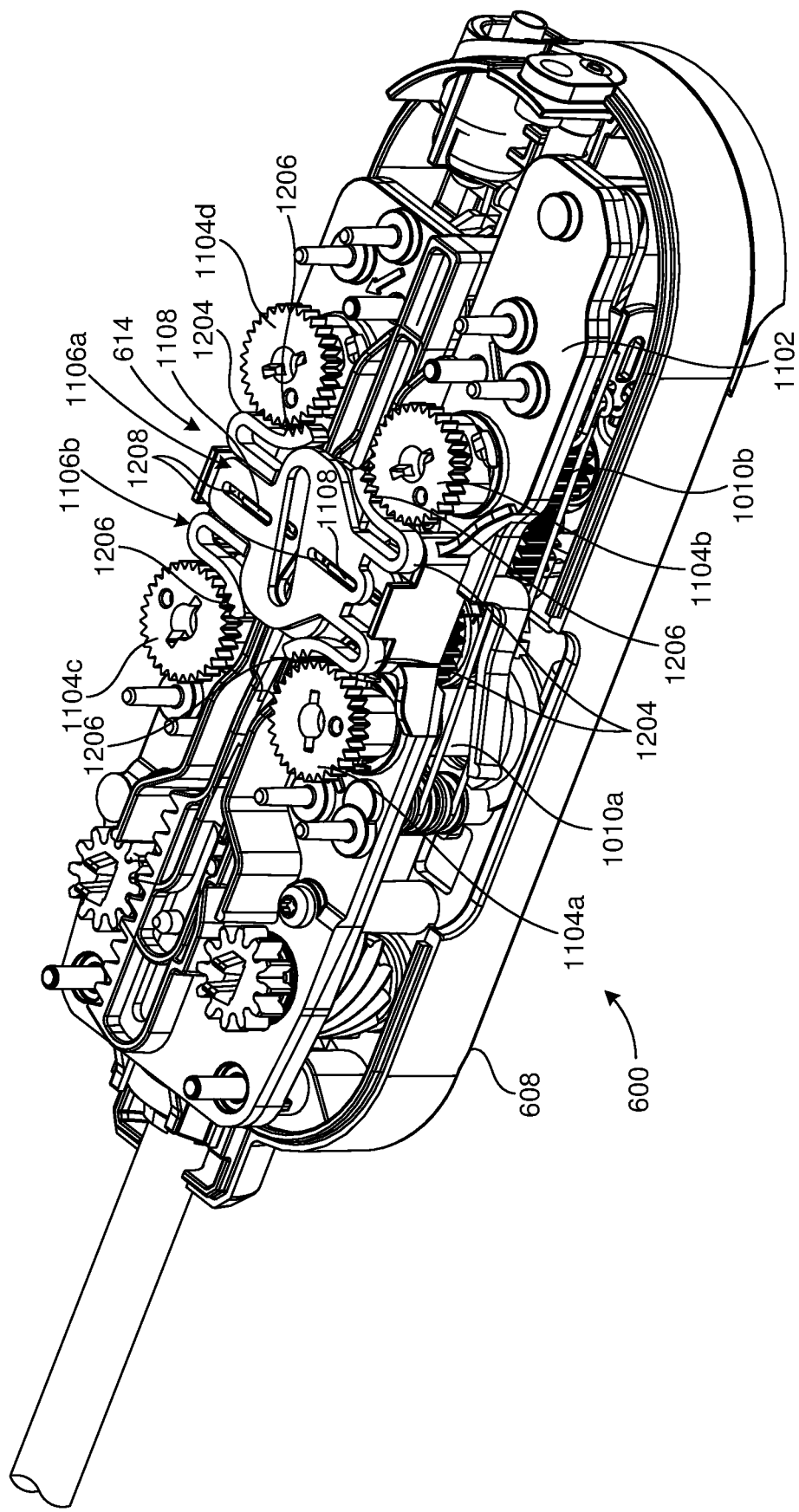
FIG. 11 is another isometric exposed view of the interior of the drive housing of the surgical tool of FIG. 6.

FIG. 11 is another isometric exposed view of the interior of the drive housing 608 that shows the internal component parts of the manual release assembly 614, according to one or more embodiments. The release switch 616 (FIG. 6) is not shown in FIG. 11 to enable viewing and discussion of the internal parts of the manual release assembly 614. As illustrated, a chassis 1102 is mounted within the drive housing 608 to support various internal component parts of the surgical tool 600, including the internal component parts of the manual release assembly 614.

Besides the release switch 616 (FIG. 6), the manual release assembly 614 further includes a first release gear 1104*a*, a second release gear 1104*b*, a third release gear 1104*c*, and a fourth release gear 1104*d*. The first release gear 1104*a* may be coupled to or form an integral extension of the first drive cable capstan 1010*a*, the second release gear 1104*b* may be coupled to or form an integral extension of the second drive cable capstan 1010*b*, the third release gear 1104*c* may be coupled to or form an integral extension of the third drive cable capstan 1010*c* (obscured in FIG. 11), and the fourth release gear 1104*d* may be coupled to or form an integral extension of the fourth drive cable capstan 1010*d* (obscured in FIG. 11). The drive cable capstans 1010*a-d* are engaged with the associated release gears 1104*a-d* such that movement (rotation) of a given drive cable capstan 1010*a-d* correspondingly moves (rotates) its associated release gear 1104*a-d* in the same angular direction, and vice versa.

The manual release assembly 614 may also include a first release plate 1106*a* and a second release plate 1106*b*. In the illustrated embodiment, the second release plate 1106*b* rests on the chassis 1102, and the first release plate 1106*a* rests on top of the second release plate 1106*b*. The first and second release plates 1106*a,b* are configured to slidingly engage each other in opposing lateral directions when the manual release assembly 614 transitions between the disengaged and engaged positions.

Figure 12:
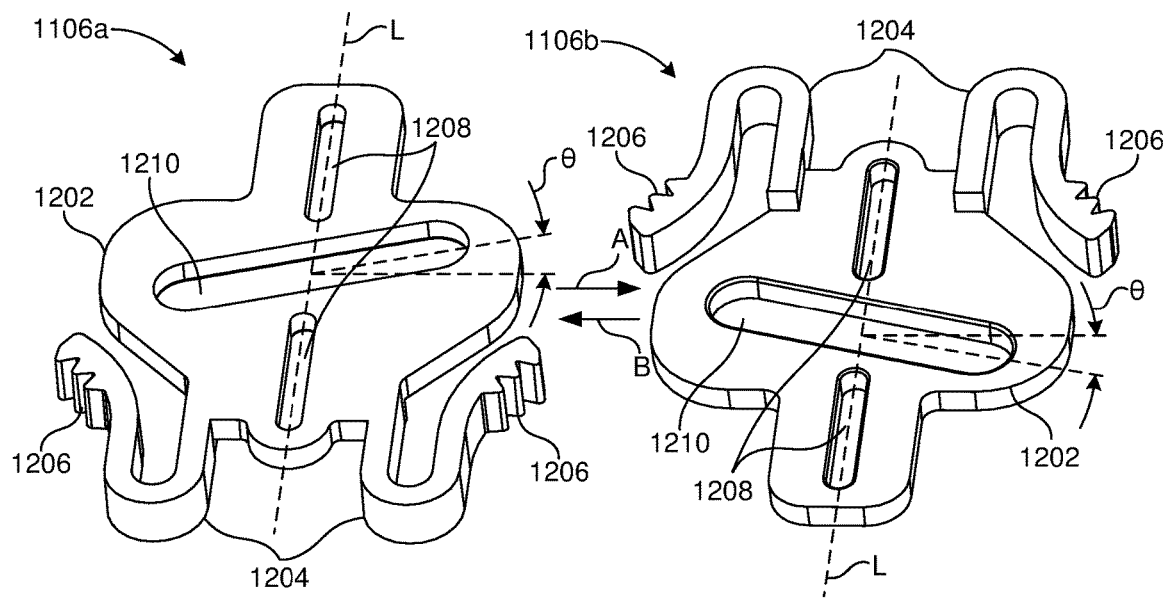
FIG. 12 is an isometric view of the first and second release plates of FIG. 11.

FIG. 12 is an isometric view of the first and second release plates 1106*a,b*, according to one or more embodiments. In such embodiments, the release plates 1106*a,b* are essentially mirror images of each other and configured to mate with each other as the first release plate 1106*a* rests atop the second release plate 1106*b*. As illustrated, each release plate 1106*a,b* comprises a generally planar body 1202 that includes a pair of arms 1204 that extend from the body 1202. A geared surface 1206 may be provided and otherwise defined on each arm 1204. In the illustrated embodiment, the geared surface 1206 is defined on the end of each arm 1204, but could alternatively be defined at any other location on the arms 1204, without departing from the scope of the disclosure.

The first and second release plates 1106*a,b* may be made of a variety of materials including, not limited to, a metal, a plastic, a composite material, and any combination thereof. In at least one embodiment, the material of the first and second release plates 1106*a,b* may comprise a flexible material that allows the arms 1204 to flex during use. This may prove advantageous as the geared surface 1206 on each arm 1204 is configured to mate with a corresponding one of the release gears 1104*a-d* (FIG. 11), and a flexible material will allow the gearing to mate properly during operation.

The body 1202 of each release plate 1106*a,b* may also provide and otherwise define one or more lateral slots 1208 that extend between the top and bottom surfaces of the body 1202. In the illustrated embodiment, two lateral slots 1208 are provided in each release plate 1106*a,b*. The lateral slots 1208 on each body 1202 are collinear along a lateral axis L. Moreover, when the first release plate 1106*a* rests atop the second release plate 1106*b* in a mated configuration, the lateral axes L align such that the lateral slots 1208 of each release plate 1106*a,b* align with each other along a plane that passes through the lateral axes L.

The body 1202 of each release plate 1106*a,b* may further provide and otherwise define an angled slot 1210 that extends at an angle θ offset from perpendicular to the lateral axis L, for example, the angle θ may be measured relative to a perpendicular axis W that is orthogonal to the lateral axis L. The angled slots 1210 of each release plate 1106*a,b* extend at equal but opposite angles. More particularly, the angle θ of the first release plate 1106*a* is a positive angle, while the angle θ of the second release plate 1106*b* is a negative angle of the same magnitude. For example, if the angle θ of the first release plate 1106*a* is 30° relative to perpendicular, the angle θ of the second release plate 1106*b* would be −30° relative to perpendicular. As a result, the angled slots 1210 diverge from each other in a first longitudinal direction A, and converge toward each other in a second longitudinal direction B opposite the first longitudinal direction A. Since the release plates 1106a,b are essentially mirror images of each other, however, the angle θ of each release plate 1106a,b may be substantially the same, depending on its relative orientation with the other release plate 1106a,b.

Referring again to FIG. 11, the first and second release plates 1106a,b may be positioned on the chassis 1102 such that one or more guide pins 1108 provided by the chassis 1102 are received into the lateral slot(s) 1208 provided by each release plate 1106a,b. In the illustrated embodiment, the chassis 1102 provides two guide pins 1108, each of which are received into the aligned lateral slots 1208 of the stacked release plates 1106a,b. The guide pins 1108 may help guide the release plates 1106a,b in relative lateral movement while the manual release assembly 614 moves between the disengaged and engaged positions.

When the manual release assembly 614 moves to the engaged position, each arm 1204 of the release plates 1106a,b may be configured and otherwise positioned to interact with a corresponding one of the release gears 1104a-d. More specifically, the geared surfaces 1206 of the arms 1204 of the first release plate 1106a may be configured to mesh and interact with the first and second release gears 1104a,b when the manual release assembly 614 moves to the engaged position. In contrast, the geared surfaces 1206 of the arms 1204 of the second release plate 1106b may be configured to mesh and interact with the third and fourth release gears 1104c,d when the manual release assembly 614 moves to the engaged position. The manual release assembly 614, however, is shown in FIG. 11 in the disengaged position, where the geared surfaces 1206 are offset from and do not engage any of the release gears 1104a-d, which allows the surgical tool 600 to operate as normal.

Figure 13:
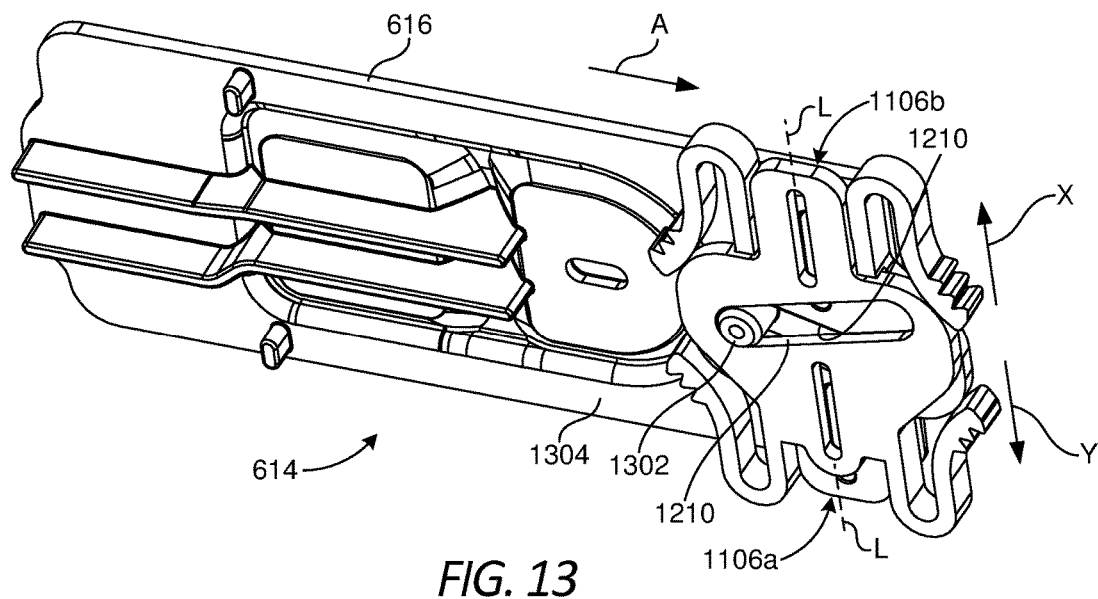
FIG. 13 is an isometric bottom view of a portion of the manual release assembly of FIGS. 6 and 11.

FIG. 13 is an isometric bottom view of a portion of the manual release assembly 614, according to one or more embodiments. More specifically, FIG. 13 depicts an isometric bottom view of the release switch 616 interacting and mating with the first and second release plates 1106a,b. As illustrated, a transition pin 1302 extends from a bottom surface 1304 of the release switch 616 and may be configured to extend through the angled slot 1210 of each release plate 1106a,b when the release plates 1106a,b are in the mated relationship.

Moving the release switch 616 in the first longitudinal direction A relative to the release plates 1106a,b correspondingly moves the transition pin 1302 in the same direction within the angled slots 1210. Because of the oppositely angled configuration of the angled slots 1210, as the release switch 616 moves in the first longitudinal direction A, the transition pin 1302 will urge the release plates 1106a,b to translate (transition) laterally with respect to each other along the lateral axis L. More specifically, moving the transition pin 1302 through the angled slots 1210 in the first longitudinal direction A will urge the first release plate 1106a to move along the lateral axis L in a first lateral direction X, and simultaneously urge the second release plate 1106b to move along the lateral axis L in a second lateral direction Y opposite the first lateral direction X. The first and second lateral directions X, Y may each be orthogonal to the first longitudinal direction A.

Figure 14:
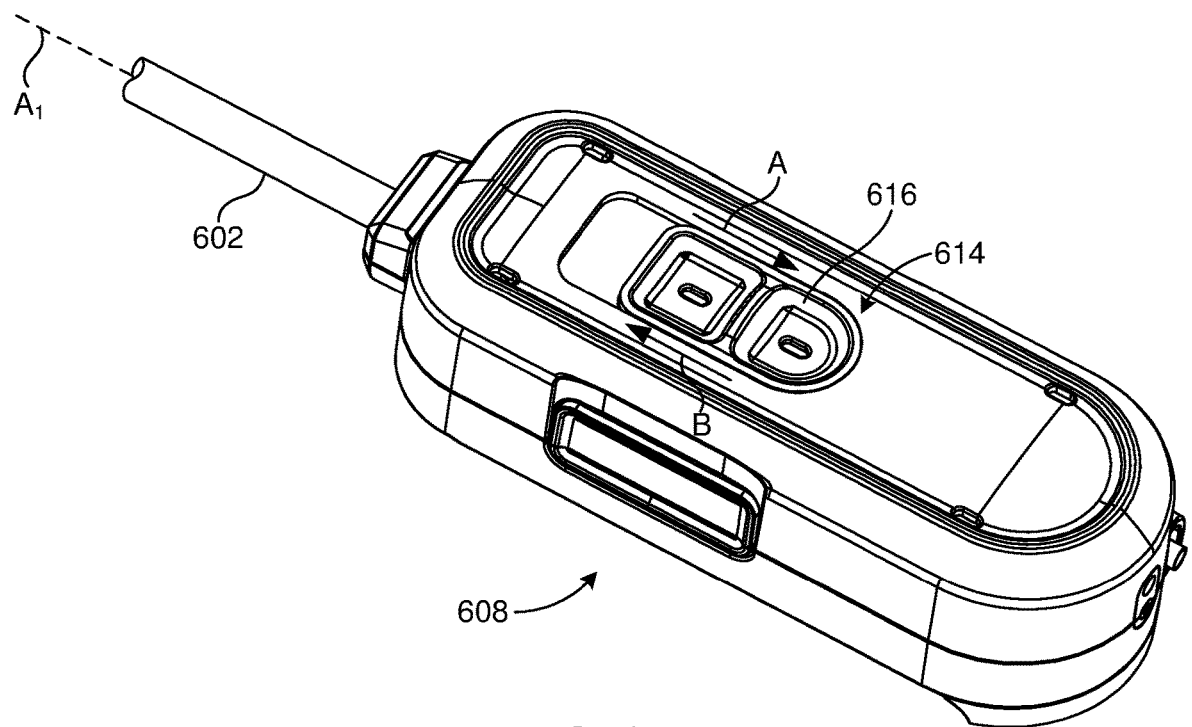
FIG. 14 is an isometric view of the drive housing with the manual release assembly of FIGS. 6 and 11 actuated.

FIG. 14 is an isometric view of the drive housing 608 with the manual release assembly 614 having been actuated or otherwise enabled. More specifically, the release switch 616 is shown having transitioned from the disengaged position of FIG. 6 to the engaged position. To transition the release switch 616 to the engaged position, a user (e.g., a surgeon) may manually engage and move the release switch 616 in the first longitudinal direction A, such as with a finger. The first longitudinal direction A is aligned with the longitudinal axis $A_1$ of the shaft 602. Moving the release switch 616 to the engaged position results in manual articulation of the end effector 604 (FIGS. 6 and 8) and, more particularly, opening of the jaws 610, 612 (FIGS. 6 and 8).

As will be appreciated, the manual release assembly 614 is reversible. To transition the release switch 616 back to the disengaged position, the user may manually engage and move the release switch 616 in the second longitudinal direction B.

Figure 15:
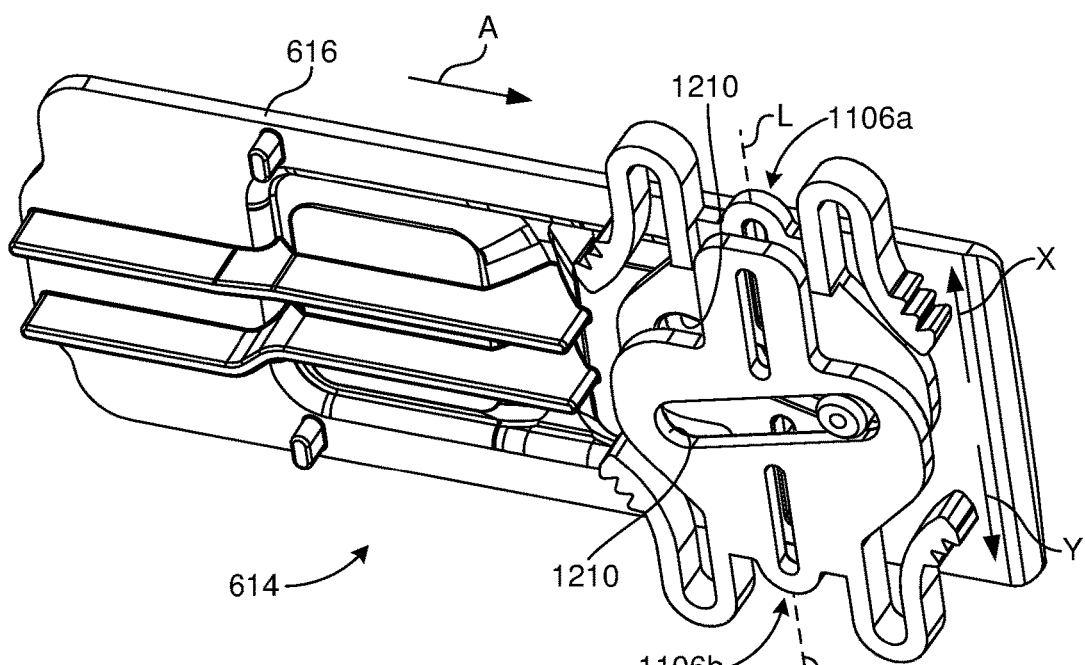
FIG. 15 is another isometric bottom view of a portion of the manual release assembly of FIGS. 6 and 11.

FIG. 15 is another isometric bottom view of a portion of the manual release assembly 614, according to one or more embodiments. More specifically, FIG. 15 depicts an isometric bottom view of the release switch 616 interacting and mating with the first and second release plates 1106a,b, where the release switch 616 has been moved to the engaged position. As the release switch 616 moves in the first longitudinal direction A toward the engaged position, the transition pin 1302 also moves in the same direction within and slidingly engages the angled slots 1210. Moreover, because of the oppositely angled configuration of the angled slots 1210, the transition pin 1302 urges the first release plate 1106a to move along the lateral axis L in the first lateral direction X and simultaneously urges the second release plate 1106b to move along the lateral axis L in the opposite second lateral direction Y.

Figure 16:
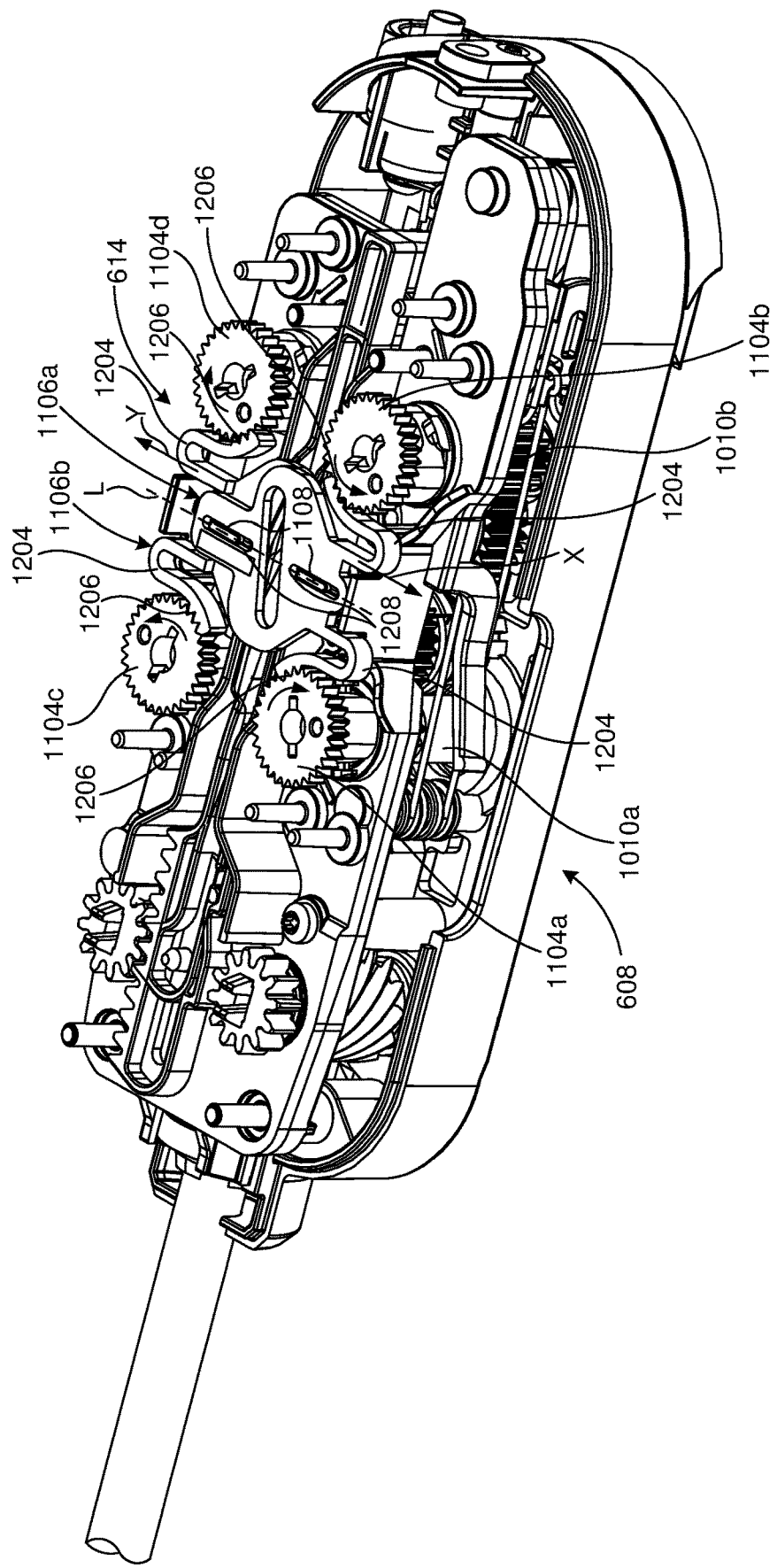
FIG. 16 is an isometric exposed view of the interior of the drive housing showing the manual release assembly having been actuated.

FIG. 16 is an isometric exposed view of the interior of the drive housing 608 showing the manual release assembly 614 having been actuated or enabled. The release switch 616 (FIGS. 6 and 13-15) is again not shown to enable viewing and description of the internal parts of the manual release assembly 614 when the release switch 616 is moved to the engaged position (see FIG. 14). As discussed with reference to FIGS. 14 and 15, the manual release assembly 614 is actuated by transitioning the release switch 616 to the engaged position, which causes the first release plate 1106a to move in the first lateral direction X and the second release plate 1106b to move in the second lateral direction Y opposite the first lateral direction X. The guide pins 1108 received into the lateral slots 1208 provided by each release plate 1106a,b help maintain the first and second release plates 1106a,b aligned along the lateral axis L (e.g., along a plane passing through the lateral axis L). The guide pins 1108 slidingly engage the aligned lateral slots 1208 as the first release plate 1106a moves in the first lateral direction X and the second release plate 1106b moves in the second lateral direction Y.

Moving the first release plate 1106a in the first lateral direction X allows the arms 1204 of the first release plate 1106a to come into contact with the first and second release gears 1104a,b. More specifically, the geared surfaces 1206 of the arms 1204 of the first release plate 1106a mesh and interact with the first and second release gears 1104a,b, and the arms 1204 may be flexible to ensure proper gear tooth engagement. Upon engagement as the first release plate 1106a moves in the first lateral direction X, the first release gear 1104a is rotated in a clockwise direction while the second release gear 1104b is rotated in a counter-clockwise direction. Rotating the first and second release gears 1104a,b in clockwise and counter-clockwise directions, respectively, correspondingly rotates the first and second drive cable capstans 1010a,b, respectively, in the same directions.

Similarly, moving the second release plate 1106b in the second lateral direction Y allows the arms 1204 of the second release plate 1106b to come into contact with the third and fourth release gears 1104*c,d*. More specifically, the geared surfaces 1206 of the arms 1204 of the second release plate 1106*b* mesh and interact with the third and fourth release gears 1104*c,d*, and the arms 1204 may be flexible to ensure proper gear tooth engagement. Upon engagement as the second release plate 1106*b* moves in the second lateral direction Y, the third release gear 1104*c* is rotated in a counter-clockwise direction while the fourth release gear 1104*d* is rotated in a clockwise direction. Rotating the third and fourth release gears 1104*c,d* in counter-clockwise and clockwise directions, respectively, correspondingly rotates the third and fourth drive cable capstans 1010*c,d* (obscured in FIG. 11, see FIG. 10), respectively, in the same directions.

Rotating the first and second drive cable capstans 1010*a,b* (FIG. 10) in the clockwise and counter-clockwise directions, respectively, and simultaneously rotating the third and fourth drive cable capstans 1010*c,d* (FIG. 10) in counter-clockwise and clockwise directions, respectively, results in articulation of the end effector 604 (FIGS. 6 and 8). More specifically, such rotation of the drive cable capstans 1010*a-d* will cause the jaws 610, 612 to open. In some embodiments, the amount of rotation assumed by the drive cable capstans 1010*a-d* as acted upon by the first and second release plates 1106*a,b* moving in the first and second lateral directions X, Y may cause the jaws 610, 612 to open between about 10° and about 30°, where each jaw 610, 612 moves between about 5° and about 15° relative to one another. As will be appreciated, design adjustments to the manual release assembly 614 may alter the maximum opening angle of the jaws 610, 612. Moreover, as indicated above, the manual release assembly 614 is reversible by manually moving the release switch 616 (FIGS. 6 and 13-15) back to the disengaged position (i.e., in the second longitudinal direction B), which manually closes the jaws 610, 612 once again.

Accordingly, the manual release assembly 614 may provide a manual over-ride intervention mechanism that can be included in the surgical tool 600 (FIG. 6) to allow for a "bail-out" function that releases grasped tissue. This may prove advantageous in the event of an electrical disruption that renders the surgical tool 600 inoperable and thus allows the user to release any grasped tissue and remove the surgical tool 600. This may also prove advantageous in cleaning and/or sterilizing the surgical tool 600 where a user is able to manually open the jaws 610, 612 (FIGS. 6 and 8).

Figure 17:
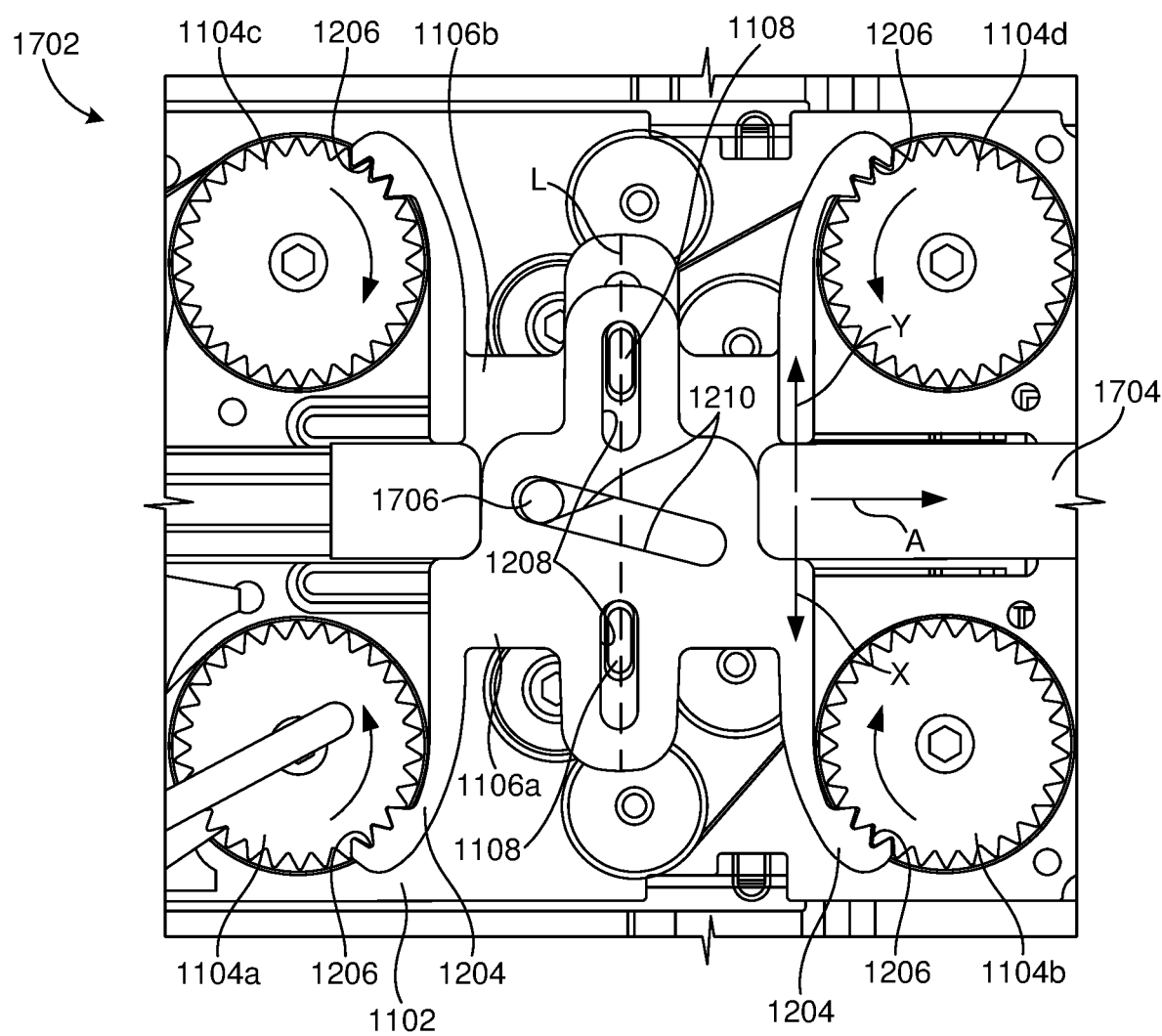
FIG. 17 is a top view of another example manual release assembly.

FIG. 17 is a top view of another example manual release assembly 1702, according to one or more embodiments. The manual release assembly 1702 may be similar in some respects to the manual release assembly 614 described herein above and therefore may be best understood with reference thereto, where like numerals will represent like components not described again in detail. Similar to the manual release assembly 614, the manual release assembly 1702 may be manually actuated by a user (e.g., a surgeon) to override the cable driven system and thereby manually articulate an end effector (e.g., the end effector 604 of FIGS. 6 and 8). Moreover, similar to the manual release assembly 614, the manual release assembly 1702 may include the first release plate 1106*a* and the second release plate 1106*b*, where the second release plate 1106*b* rests on the chassis 1102, and the first release plate 1106*a* rests on top of the second release plate 1106*b*.

Unlike the manual release assembly 614, however, the manual release assembly 1702 includes a release switch 1704 in the form of a translating shaft that can be manually moved from a disengaged position to an engaged position by a user to enable (actuate) the manual release assembly 1702.

In some embodiments, the release switch 1704 may extend out an end of the drive housing 606 (FIG. 6) and thereby provide a location for a user to grasp and manipulate the release switch 1704.

The release switch 1704 includes a transition pin 1706 that extends through the angled slot 1210 of each release plate 1106*a,b*. Moving the release switch 1704 in the first longitudinal direction A relative to the release plates 1106*a,b* correspondingly moves the transition pin 1706 in the same direction within the angled slots 1210. The angled slots 1210 in the illustrated release plates 1106*a,b*, however, are angled oppositely as compared to the angled slots 1210 depicted in FIG. 12. More specifically, if the angled slot 1210 of the first release plate 1106*a* extended at 30° in FIG. 12, the angled slot 1210 of the first release plate 1106*a* in FIG. 17 now extends at −30°. Similarly, if the angled slot 1210 of the second release plate 1106*b* extended at −30° in FIG. 12, the angled slot 1210 of the second release plate 1106*b* in FIG. 17 now extends at 30°. This results in the release plates 1106*a,b* of FIG. 17 moving in opposite lateral directions along the lateral axis L, as compared to the embodiment of FIG. 12.

More particularly, because of the oppositely angled configuration of the angled slots 1210, as the release switch 1704 moves in the first longitudinal direction A, the transition pin 1706 will urge the release plates 1106*a,b* to translate (transition) laterally with respect to each other along the lateral axis L. Moving the transition pin 1706 through the angled slots 1210 in the first longitudinal direction A will urge the first release plate 1106*a* to move along the lateral axis L in the second lateral direction Y, and simultaneously urge the second release plate 1106*b* to move along the lateral axis L in the first lateral direction X. The guide pins 1108 received into the lateral slots 1208 provided by each release plate 1106*a,b* help maintain the first and second release plates 1106*a,b* aligned along the lateral axis L (e.g., along a plane passing through the lateral axis L) as the first release plate 1106*a* moves in the second lateral direction Y and the second release plate 1106*b* moves in the first lateral direction X.

Moving the first release plate 1106*a* in the second lateral direction Y brings the geared surfaces 1206 of the arms 1204 of the first release plate 1106*a* into meshing contact with the first and second release gears 1104*a,b*. As the first release plate 1106*a* moves in the second lateral direction Y, the first release gear 1104*a* is rotated in a counter-clockwise direction while the second release gear 1104*b* is rotated in a clockwise direction. Moreover, rotating the first and second release gears 1104*a,b* in counter-clockwise and clockwise directions, respectively, correspondingly rotates the first and second drive cable capstans 1010*a,b* (FIG. 10), respectively, in the same directions.

Similarly, moving the second release plate 1106*b* in the first lateral direction X brings the geared surfaces 1206 of the arms 1204 of the second release plate 1106*b* into meshing contact with the third and fourth release gears 1104*c,d*. As the second release plate 1106*b* moves in the first lateral direction X, the third release gear 1104*c* is rotated in a clockwise direction while the fourth release gear 1104*d* is rotated in a counter-clockwise direction. Moreover, rotating the third and fourth release gears 1104*c,d* in clockwise and counter-clockwise directions, respectively, correspondingly rotates the third and fourth drive cable capstans 1010*a,b* (FIG. 10), respectively, in the same directions.

Rotating the first and second drive cable capstans 1010*a,b* (FIG. 10) in the counter-clockwise and clockwise directions, respectively, and simultaneously rotating the third and fourth drive cable capstans 1010c,d (FIG. 10) in clockwise and counter-clockwise directions, respectively, results in articulation of the end effector 604 (FIGS. 6 and 8). More specifically, such rotation of the drive cable capstans 1010a-d will cause the jaws 610, 612 to open. Moreover, the manual release assembly 1702 is reversible by manually moving the release switch 1704 back to the disengaged position (i.e., in the second longitudinal direction B), which manually closes the jaws 610, 612 once again.

Embodiments disclosed herein include:

A. A surgical tool that includes a drive housing that houses a plurality of drive cable capstans, an elongate shaft that extends from the drive housing, an end effector operatively coupled to a distal end of the elongate shaft, a plurality of drive cables extending between the drive housing and the end effector, wherein each drive cable is associated with a corresponding one of the plurality of drive cable capstans and rotation of the plurality of drive cable capstans correspondingly moves the plurality of drive cables to articulate the end effector, and a manual release assembly coupled to the drive housing and including a release switch that is manually movable between a disengaged position and an engaged position, wherein, when the release switch is manually moved to the engaged position, the plurality of drive cable capstans are rotated to move the plurality of drive cables and thereby manually articulate the end effector.

B. A method of operating a surgical tool that includes positioning the surgical tool adjacent a patient for operation, the surgical tool including a drive housing that houses a plurality of drive cable capstans, an elongate shaft that extends from the drive housing, an end effector operatively coupled to a distal end of the elongate shaft, a plurality of drive cables extending between the drive housing and the end effector, wherein each drive cable is associated with a corresponding one of the plurality of drive cable capstans, and a manual release assembly coupled to the drive housing and including a release switch that is manually movable between a disengaged position and an engaged position. The method further including rotating one or more of the plurality of drive cable capstans and thereby correspondingly moving one or more of the plurality of drive cables to articulate the end effector, and manually moving the release switch to the engaged position and thereby rotating the plurality of drive cable capstans to move the plurality of drive cables and thereby manually articulate the end effector.

C. A method cleaning a surgical tool, the surgical tool including a drive housing that houses a plurality of drive cable capstans, an elongate shaft that extends from the drive housing, an end effector having opposing first and second jaws and being operatively coupled to a distal end of the elongate shaft, a plurality of drive cables extending between the drive housing and the end effector, wherein each drive cable is associated with a corresponding one of the plurality of drive cable capstans, and a manual release assembly coupled to the drive housing and including a release switch that is manually movable between a disengaged position and an engaged position, the method including manually moving the release switch to the engaged position and thereby rotating the plurality of drive cable capstans to move the plurality of drive cables and thereby manually move the first and second jaws to an open position, and cleaning the first and second jaws.

Each of embodiments A, B, and C may have one or more of the following additional elements in any combination: Element 1: wherein the manual release assembly further includes a plurality of release gears each coupled to a corresponding one of the plurality of drive cable capstans for rotation therewith, a first release plate arranged within the drive housing and including a first pair of arms engageable with a first two of the plurality of release gears, and a second release plate arranged within the drive housing and including a second pair of arms engageable with a second two the plurality of release gears, wherein the first and second pairs of arms are disengaged from the plurality of release gears when the release switch is in the disengaged position, and wherein, when the release switch is moved to the engaged position, the first and second pairs of arms engage and rotate the plurality of release gears, which correspondingly rotate the plurality of drive cable capstans and thereby manually articulate the end effector. Element 2: wherein a geared surface is provided on each arm of the first and second pairs of arms, and wherein the geared surface is configured to mate with a corresponding geared surface provided on each release gear. Element 3: wherein the first and second pairs of arms are flexible to ensure proper gear tooth engagement between the geared surface of arm and the corresponding geared surface provided on each release gear. Element 4: further comprising a first angled slot defined in the first release plate, a second angled slot defined in the second release plate, where the first and second angled slots are oppositely angled, and a transition pin extending from the manual release tool and into the first and second angled slots, wherein, when the release switch is moved to the engaged position, the transition pin moves through the first and second angled slots and urges the first and second release plates in opposing lateral directions such that the first and second pairs of arms engage and rotate the plurality of release gears. Element 5: further comprising a chassis arranged within the drive housing to support the first and second release plates, wherein the second release plate is positioned on the chassis and the first release plate rests atop the second release plate, one or more lateral slots defined in each of the first and second release plates, wherein the one or more lateral slots in each release plate are aligned when the first release plate rests atop the second release plate, and one or more guide pins extending from the chassis and into the one or more lateral slots, wherein the guide pins guide the first and second release plates in the opposing lateral directions. Element 6: wherein the first and second angled slots each extend at an angle offset from perpendicular to a lateral axis passing through the one or more lateral slots. Element 7: wherein the end effector includes opposing first and second jaws, and wherein manually moving the release switch to the engaged position moves the first and second jaws to an open position. Element 8: wherein the first and second jaws are opened between about 10° and about 30° relative to one another. Element 9: wherein the release switch is manually movable back to the disengaged position, and thereby moving the first and second jaws back to a closed position. Element 10: further comprising a plurality of drive gears, wherein each drive gear forms part of a corresponding one of the plurality of drive cable capstans, and a plurality of driven gears, each driven gear being positioned to be driven by a corresponding one of the plurality of drive gears, wherein each drive cable is coupled to a corresponding one of the plurality of driven gears such that rotation of the plurality of drive cable capstans correspondingly rotates the plurality of drive gears and thereby rotates the plurality of driven gears, and rotation of the plurality of driven gears moves the plurality of drive cables to articulate the end effector. Element 11: wherein the end effector is selected from the group consisting of forceps, a tissue grasper, a needle driver, scissors, an electro cautery tool, a stapler, a clip applier, and any combination thereof.

Element 12: wherein the manual release assembly further includes a plurality of release gears each coupled to a corresponding one of the plurality of drive cable capstans for rotation therewith, a first release plate arranged within the drive housing and including a first pair of arms, and a second release plate arranged within the drive housing and including a second pair of arms, and wherein manually moving the release switch to the engaged position further comprises engaging the first pair of arms against a first two of the plurality of release gears and thereby rotating the first two of the plurality of release gears, engaging the second pair of arms against a second two of the plurality of release gears and thereby rotating the second two of the plurality of release gears, and rotating the plurality of drive cable capstans to manually articulate the end effector as the plurality of release gears are rotated by the first and second pairs of arms. Element 13: wherein a geared surface is provided on each arm of the first and second pairs of arms, the method further comprising mating the geared surface on each arm with a corresponding geared surface provided on each release gear. Element 14: wherein the first and second pairs of arms are flexible to ensure proper gear tooth engagement between the geared surface of arm and the corresponding geared surface provided on each release gear. Element 15: wherein the first release plate defines a first angled slot, the second release plate defines a second angled slot, and a transition pin extends from the manual release tool and into the first and second angled slots, and wherein manually moving the release switch to the engaged position further comprises moving the transition pin through the first and second angled slots, the first and second angled slots being oppositely angled, and urging the first and second release plates in opposing lateral directions with the transition pin such that the first and second pairs of arms engage and rotate the plurality of release gears. Element 16: wherein the end effector includes opposing first and second jaws, and wherein manually moving the release switch to the engaged position comprises moving the first and second jaws to an open position. Element 17: further comprising moving the release switch back to the disengaged position and thereby moving the first and second jaws back to a closed position.

By way of non-limiting example, exemplary combinations applicable to A, B, and C include: Element 1 with Element 2; Element 1 with Element 3; Element 1 with Element 4; Element 4 with Element 5; Element 5 with Element 6; Element 7 with Element 8; Element 7 with Element 9; Element 12 with Element 13; Element 12 with Element 14; Element 12 with Element 15; and Element 16 with Element 17.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical tool, comprising:
    a drive housing that houses a plurality of drive cable capstans;
    an elongate shaft that extends from the drive housing;
    an end effector operatively coupled to a distal end of the elongate shaft and including opposing first and second jaws;
    a plurality of drive cables extending from the drive housing to the end effector, wherein each drive cable is associated with a corresponding one of the plurality of drive cable capstans and rotation of the plurality of drive cable capstans correspondingly moves the plurality of drive cables to move the first and second jaws between open and closed positions; and
    a manual release assembly coupled to the drive housing and including a release switch that is manually movable between a disengaged position and an engaged position, wherein, when the release switch is manually moved to the engaged position, the plurality of drive cable capstans are rotated to move the plurality of drive cables and thereby manually move the first and second jaws to the open position.

2. The surgical tool of claim 1, wherein the manual release assembly further includes:
    a plurality of release gears each coupled to a corresponding one of the plurality of drive cable capstans for rotation therewith;
    a first release plate arranged within the drive housing and including a first pair of arms engageable with a first two of the plurality of release gears; and
    a second release plate arranged within the drive housing and including a second pair of arms engageable with a second two of the plurality of release gears, wherein the first and second pairs of arms are disengaged from the plurality of release gears when the release switch is in the disengaged position, and wherein, when the release switch is moved to the engaged position, the first and second pairs of arms engage and rotate the plurality of release gears, which correspondingly rotate the plurality of drive cable capstans.

3. The surgical tool of claim 2, wherein a geared surface is provided on each arm of the first and second pairs of arms, and wherein the geared surface is configured to mate with a corresponding geared surface provided on each release gear.

4. The surgical tool of claim 2, wherein the first and second pairs of arms are flexible to ensure proper gear tooth engagement between the geared surface of arm and the corresponding geared surface provided on each release gear.

5. The surgical tool of claim 2, further comprising:
a first angled slot defined in the first release plate;
a second angled slot defined in the second release plate, where the first and second angled slots are oppositely angled; and
a transition pin extending from the release switch and into the first and second angled slots,
wherein, when the release switch is moved to the engaged position, the transition pin moves through the first and second angled slots and urges the first and second release plates in opposing lateral directions such that the first and second pairs of arms engage and rotate the plurality of release gears.

6. The surgical tool of claim 5, further comprising:
a chassis arranged within the drive housing to support the first and second release plates, wherein the second release plate is positioned on the chassis and the first release plate rests atop the second release plate;
one or more lateral slots defined in each of the first and second release plates, wherein the one or more lateral slots in each release plate are aligned when the first release plate rests atop the second release plate; and
one or more guide pins extending from the chassis and into the one or more lateral slots, wherein the guide pins guide the first and second release plates in the opposing lateral directions.

7. The surgical tool of claim 6, wherein the first and second angled slots each extend at an angle offset from perpendicular to a lateral axis passing through the one or more lateral slots.

8. The surgical tool of claim 1, wherein the first and second jaws are opened between 10° and 30° relative to one another when moved to the open position.

9. The surgical tool of claim 1, wherein the release switch is manually movable back to the disengaged position, which results in the first and second jaws moving to the closed position.

10. The surgical tool of claim 1, further comprising:
a plurality of drive gears, wherein each drive gear forms part of a corresponding one of the plurality of drive cable capstans; and
a plurality of driven gears, each driven gear being positioned to be driven by a corresponding one of the plurality of drive gears,
wherein each drive cable is coupled to a corresponding one of the plurality of driven gears such that rotation of the plurality of drive cable capstans correspondingly rotates the plurality of drive gears and thereby rotates the plurality of driven gears, and rotation of the plurality of driven gears moves the plurality of drive cables.

11. The surgical tool of claim 1, wherein the end effector is selected from the group consisting of forceps, a tissue grasper, a needle driver, scissors, an electro cautery tool, a stapler, a clip applier, and any combination thereof.

12. A method of operating a surgical tool, comprising:
positioning the surgical tool adjacent a patient for operation, the surgical tool including:
a drive housing that houses a plurality of drive cable capstans;
an elongate shaft that extends from the drive housing;
an end effector operatively coupled to a distal end of the elongate shaft and including opposing first and second jaws;
a plurality of drive cables extending from the drive housing to the end effector, wherein each drive cable is associated with a corresponding one of the plurality of drive cable capstans; and
a manual release assembly coupled to the drive housing and including a release switch that is manually movable between a disengaged position and an engaged position;
rotating one or more of the plurality of drive cable capstans and thereby correspondingly moving one or more of the plurality of drive cables to move the first and second jaws between open and closed positions; and
manually moving the release switch to the engaged position and thereby rotating the plurality of drive cable capstans to move the plurality of drive cables and thereby manually move the first and second jaws to the open position.

13. The method of claim 12, wherein the manual release assembly further includes a plurality of release gears each coupled to a corresponding one of the plurality of drive cable capstans for rotation therewith, a first release plate arranged within the drive housing and including a first pair of arms, and a second release plate arranged within the drive housing and including a second pair of arms, and
wherein manually moving the release switch to the engaged position further comprises:
engaging the first pair of arms against a first two of the plurality of release gears and thereby rotating the first two of the plurality of release gears;
engaging the second pair of arms against a second two of the plurality of release gears and thereby rotating the second two of the plurality of release gears; and
rotating the plurality of drive cable capstans as the plurality of release gears are rotated by the first and second pairs of arms.

14. The method of claim 13, wherein a geared surface is provided on each arm of the first and second pairs of arms, the method further comprising mating the geared surface on each arm with a corresponding geared surface provided on each release gear.

15. The method of claim 13, wherein the first and second pairs of arms are flexible to ensure proper gear tooth engagement between the geared surface of arm and the corresponding geared surface provided on each release gear.

16. The method of claim 13, wherein the first release plate defines a first angled slot, the second release plate defines a second angled slot, and a transition pin extends from the manual release tool and into the first and second angled slots, and wherein manually moving the release switch to the engaged position further comprises:
moving the transition pin through the first and second angled slots, the first and second angled slots being oppositely angled; and urging the first and second release plates in opposing lateral directions with the transition pin such that the first and second pairs of arms engage and rotate the plurality of release gears.

17. The method of claim 12, further comprising moving the release switch back to the disengaged position and thereby moving the first and second jaws to the closed position.

18. A method of cleaning a surgical tool, the surgical tool including a drive housing that houses a plurality of drive cable capstans, an elongate shaft that extends from the drive housing, an end effector including opposing first and second jaws and being operatively coupled to a distal end of the elongate shaft, a plurality of drive cables extending from the drive housing to the end effector, wherein each drive cable is associated with a corresponding one of the plurality of drive cable capstans, and a manual release assembly coupled to the drive housing and including a release switch that is manually movable between a disengaged position and an engaged position, the method comprising:
  manually moving the release switch to the engaged position and thereby rotating the plurality of drive cable capstans to move the plurality of drive cables and thereby manually move the first and second jaws to an open position; and
  cleaning the first and second jaws.

* * * * *